US009867991B2

(12) United States Patent
Parker

(10) Patent No.: US 9,867,991 B2
(45) Date of Patent: Jan. 16, 2018

(54) PHYSICIAN PROGRAMMER WITH ENHANCED GRAPHICAL USER INTERFACE, AND ASSOCIATED SYSTEMS AND METHODS

(71) Applicant: Nevro Corporation, Menlo Park, CA (US)

(72) Inventor: Jon Parker, San Jose, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

(21) Appl. No.: 14/447,095

(22) Filed: Jul. 30, 2014

(65) Prior Publication Data
US 2015/0039047 A1  Feb. 5, 2015

Related U.S. Application Data

(60) Provisional application No. 61/860,817, filed on Jul. 31, 2013.

(51) Int. Cl.
*A61N 1/372* (2006.01)
*A61N 1/36* (2006.01)

(52) U.S. Cl.
CPC ..... *A61N 1/37247* (2013.01); *A61N 1/36071* (2013.01); *A61N 1/36132* (2013.01); *A61N 1/36167* (2013.01); *A61N 1/37252* (2013.01); *A61N 1/36185* (2013.01); *A61N 1/37264* (2013.01)

(58) Field of Classification Search
CPC .................................. A61N 1/36; A61N 1/372
USPC ....................................................... 607/45, 59
See application file for complete search history.

(56) References Cited

U.S. PATENT DOCUMENTS

| 3,195,540 A | 7/1965 | Waller |
| 4,024,875 A | 5/1977 | Putzke |
| 4,096,866 A | 6/1978 | Fischell |

(Continued)

FOREIGN PATENT DOCUMENTS

| WO | WO-0160450 A1 | 8/2001 |
| WO | WO-03011361 A2 | 2/2003 |

(Continued)

OTHER PUBLICATIONS

Huxely et al., "Excitation and Conduction in Nerve: Quantitative Analysis," Science, Sep. 11, 1964; 145: 1154-9.

(Continued)

*Primary Examiner* — Carl H Layno
*Assistant Examiner* — Jon Eric C Morales
(74) *Attorney, Agent, or Firm* — Perkins Coie LLP

(57) ABSTRACT

Devices for controlling spinal cord modulation for inhibiting pain, and associated systems and methods, including controllers for modulation program recommendation are disclosed. A particular embodiment includes receiving, from multiple computing devices, ratings for modulation programs executed by implantable medical devices for a plurality of patients, ranking the modulation programs based on the received ratings and based on at least one characteristic of the patients and the symptoms described by the patients, receiving a recommendation request for a modulation program for a particular patient; and transmitting one or more of the highest ranking modulation programs in response to the request for a modulation program for the particular patient.

11 Claims, 27 Drawing Sheets

(56) References Cited

U.S. PATENT DOCUMENTS

| | | |
|---|---|---|
| 4,232,679 A | 11/1980 | Schulman |
| 4,399,818 A | 8/1983 | Money |
| 4,441,498 A | 4/1984 | Nordling |
| 4,592,359 A | 6/1986 | Galbraith |
| 4,735,204 A | 4/1988 | Sussman et al. |
| 5,159,926 A | 11/1992 | Ljungstroem |
| 5,193,538 A | 3/1993 | Ekwall |
| 5,641,326 A | 6/1997 | Adams |
| 5,713,937 A | 2/1998 | Nappholz et al. |
| 5,769,877 A | 6/1998 | Barreras, Sr. |
| 5,891,179 A | 4/1999 | Er et al. |
| 6,052,624 A | 4/2000 | Mann |
| 6,073,049 A | 6/2000 | Alt et al. |
| 6,106,460 A | 8/2000 | Panescu et al. |
| 6,249,703 B1 | 6/2001 | Stanton et al. |
| 6,393,325 B1 | 5/2002 | Mann et al. |
| 6,438,423 B1 | 8/2002 | Rezai et al. |
| 6,516,227 B1 | 2/2003 | Meadows et al. |
| 6,609,032 B1 | 8/2003 | Woods et al. |
| 6,622,048 B1 | 9/2003 | Mann |
| 6,687,538 B1 | 2/2004 | Hrdlicka et al. |
| 6,856,315 B2 | 2/2005 | Eberlein |
| 6,909,917 B2 | 6/2005 | Woods et al. |
| 6,950,706 B2 | 9/2005 | Rodriguez et al. |
| 7,177,691 B2 | 2/2007 | Meadows et al. |
| 7,289,852 B2 | 10/2007 | Helfinstine et al. |
| 7,359,751 B1 | 4/2008 | Erickson et al. |
| 7,444,184 B2 | 10/2008 | Boveja et al. |
| 7,551,960 B2 | 6/2009 | Forsberg et al. |
| 7,623,918 B2 | 11/2009 | Goetz |
| 7,640,059 B2 | 12/2009 | Forsberg et al. |
| 7,657,319 B2 | 2/2010 | Goetz et al. |
| 7,747,330 B2 | 6/2010 | Nolan et al. |
| 7,826,902 B2 | 11/2010 | Stone et al. |
| 7,848,802 B2 | 12/2010 | Goetz et al. |
| 2004/0034394 A1 | 2/2004 | Woods et al. |
| 2004/0093093 A1 | 5/2004 | Andrews |
| 2004/0167584 A1 | 8/2004 | Carroll et al. |
| 2004/0199214 A1 | 10/2004 | Merfeld et al. |
| 2005/0245987 A1 | 11/2005 | Woods et al. |
| 2006/0074450 A1 | 4/2006 | Boveja et al. |
| 2006/0190048 A1 | 8/2006 | Gerber |
| 2006/0241720 A1 | 10/2006 | Woods et al. |
| 2006/0241721 A1 | 10/2006 | Kothandaraman et al. |
| 2006/0259098 A1 | 11/2006 | Erickson |
| 2007/0049991 A1 | 3/2007 | Klostermann et al. |
| 2007/0179559 A1 | 8/2007 | Giftakis et al. |
| 2007/0203537 A1 | 8/2007 | Goetz et al. |
| 2007/0203538 A1 | 8/2007 | Stone et al. |
| 2007/0203541 A1 | 8/2007 | Goetz et al. |
| 2007/0203543 A1 | 8/2007 | Stone et al. |
| 2007/0203545 A1 | 8/2007 | Stone et al. |
| 2007/0213783 A1 | 9/2007 | Pless |
| 2007/0213790 A1 | 9/2007 | Nolan et al. |
| 2007/0244520 A1 | 10/2007 | Ferren et al. |
| 2007/0260290 A1 | 11/2007 | Hara et al. |
| 2007/0270921 A1 | 11/2007 | Strother et al. |
| 2007/0276450 A1 | 11/2007 | Meadows et al. |
| 2007/0282390 A1 | 12/2007 | Shuros |
| 2008/0103570 A1 | 5/2008 | Gerber |
| 2008/0215119 A1 | 9/2008 | Woods et al. |
| 2008/0234791 A1 | 9/2008 | Arle et al. |
| 2009/0204173 A1 | 8/2009 | Fang et al. |
| 2010/0010585 A1* | 1/2010 | Davis ................... A61B 5/1116 607/62 |
| 2010/0137938 A1 | 6/2010 | Kishawi et al. |
| 2010/0222845 A1* | 9/2010 | Goetz ............................ 607/59 |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2011/0022114 A1 | 1/2011 | Navarro |
| 2011/0137371 A1* | 6/2011 | Giftakis et al. ................. 607/45 |

FOREIGN PATENT DOCUMENTS

| | | |
|---|---|---|
| WO | WO-2007035925 A2 | 3/2007 |
| WO | WO-2008039982 A2 | 4/2008 |
| WO | WO-2008121891 A1 | 10/2008 |

OTHER PUBLICATIONS

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Medtronic, "InterStim Therapy—Patient Manual," InterStim Therapy for Urinary Control, Neurological Division, 1999, 72 pages.

Medtronic, "Kinetra®, Soletra®, and Itrel® II Neurostimulators for Deep Brain Stimulation (DMS™) 8870," Program Guide for Software Version A- 2003.

Medtronic, "Test Stimulator Model 3625—Test Stimulator for Deep Brain Stimulation," Operator Manual, 2006, 72 pages.

North et al., "Spinal Cord Stimulation for Axial Low Back Pain," SPINE, vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

* cited by examiner

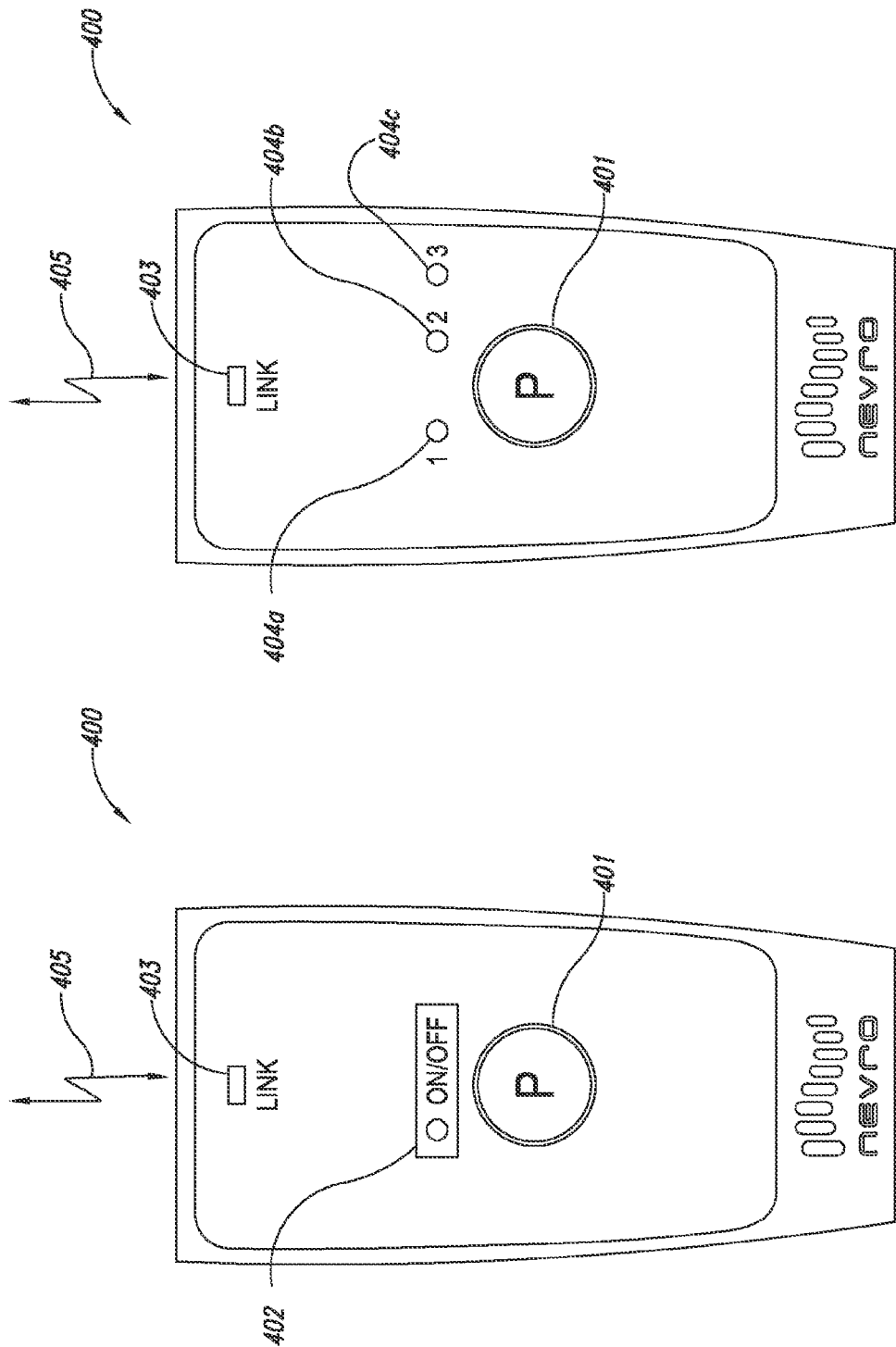

Pain Score

798

New Pain Score | Edit | Delete | Save | Quick Look... | Export

02 Jan 2012 09:30 | Baseline

| Description | None | Mild | Moderate | Severe | Very Severe | Worst Possible |
|---|---|---|---|---|---|---|

Back: 0 1 2 3 4 5 6 7 8 9 10 — 8.1

Leg: 0 1 2 3 4 5 6 7 8 9 10 — 6.5

Other: 0 1 2 3 4 5 6 7 8 9 10 — N/A

Notes:

Previous Pain Scores

| Date and Time ▲ | Treatment Stage | Back Pain Score | Leg Pain Score | Other Pain Score | Other Description |
|---|---|---|---|---|---|
| 02 Jan 2012 09:30 | Baseline | 8.1 | 6.5 | | |
| 05 Jan 2012 08:00 | Trial Follow-up | 6.0 | 5.0 | | |
| 06 Jan 2012 11:30 | Trial Follow-up | 5.1 | 5.7 | | |
| 08 Jan 2012 14:00 | Trial Follow-up | 1.5 | 0.7 | | |
| 09 Jan 2012 10:15 | Trial Follow-up | 0.5 | 0.7 | | |
| 05 Feb 2012 16:00 | Permanent | 0.8 | 0.7 | | |
| 06 Mar 2012 00:00 | Permanent Follow-up | 0.3 | 0.4 | | |

*Fig. 70*

PHYSICIAN PROGRAMMER WITH ENHANCED GRAPHICAL USER INTERFACE, AND ASSOCIATED SYSTEMS AND METHODS

CROSS-REFERENCE TO RELATED APPLICATION

The present application claims priority to U.S. Provisional Application No. 61/860,817, filed Jul. 31, 2013, entitled PHYSICIAN PROGRAMMER WITH ENHANCED GRAPHICAL USER INTERFACE, AND ASSOCIATED SYSTEMS AND METHODS, which is herein incorporated by reference in its entirety.

TECHNICAL FIELD

The present disclosure is directed generally to devices for controlling spinal cord modulation for inhibiting pain, and associated systems and methods, including spinal cord modulation system controllers and graphical user interfaces.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. In pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. While this may be the case for many patients, many other patients may report less beneficial effects and/or results. Accordingly, there remains a need for improved techniques and systems for addressing patient pain.

BRIEF DESCRIPTION OF THE DRAWINGS

FIGS. 4A-4C are schematics illustrating versions of patient-operated controller in accordance with particular embodiments of the present disclosure.

DETAILED DESCRIPTION

1.0 Introduction

Figure 1A:
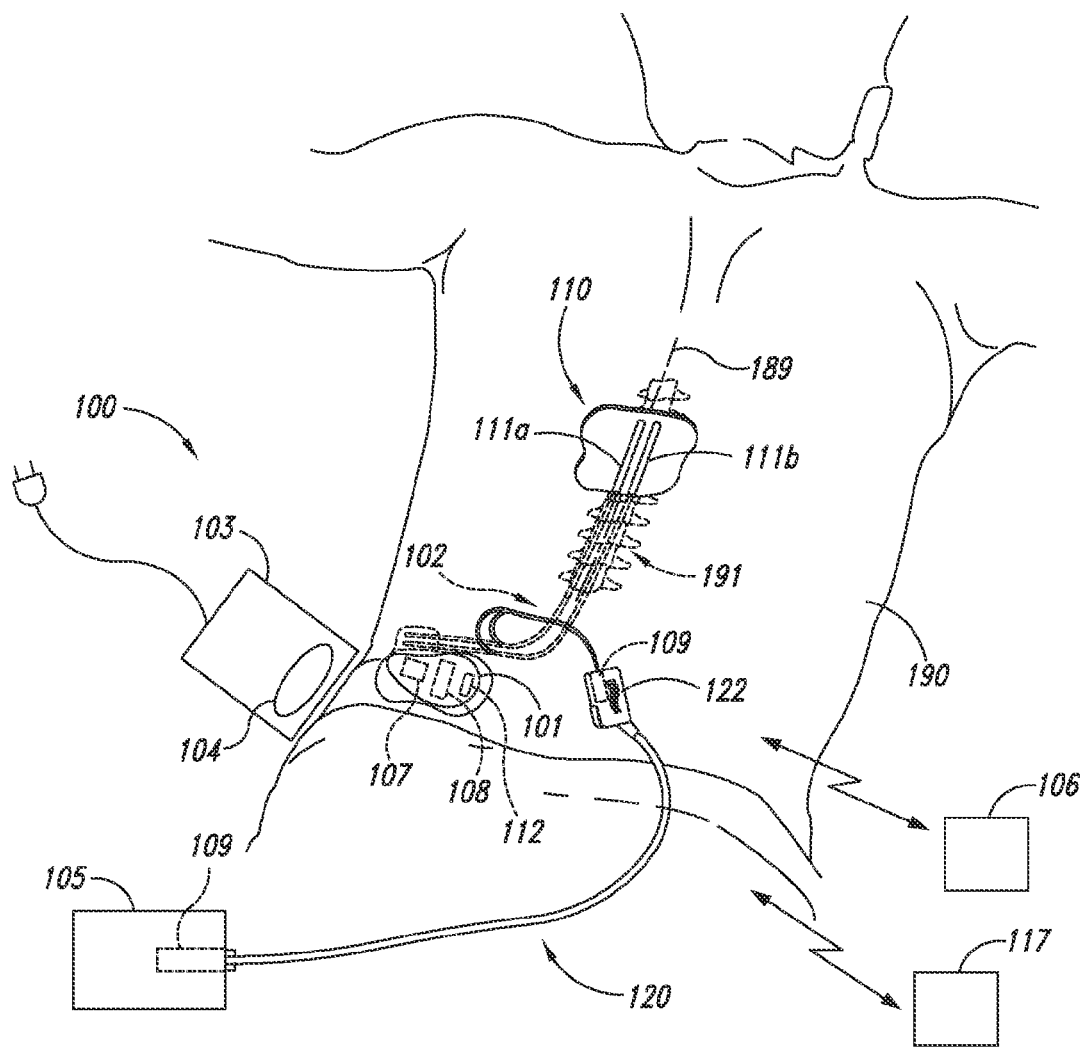
FIG. 1A is a partially schematic illustration of an implantable spinal cord modulation system positioned at the spine to deliver therapeutic signals in accordance with several embodiments of the present disclosure.

The present technology is directed generally to spinal cord modulation and associated systems and methods for inhibiting pain. In particular embodiments, waveforms in accordance with the present technology have high frequency elements or components (e.g., portions having high fundamental frequencies), and generally produce reduced or eliminated side effects. Such side effects can include unwanted motor stimulation or blocking, and/or interference with sensory functions other than the targeted pain. Several embodiments also provide simplified spinal cord modulation systems and components, and simplified procedures for the practitioner and/or the patient. Specific details of certain embodiments of the present disclosure are described below with reference to methods for modulating one or more target neural populations (e.g., nerves) or sites of a patient, and associated implantable structures for providing the modulation. Although selected embodiments are described below with reference to modulating the dorsal column, dorsal horn, dorsal root, dorsal root entry zone, and/or other particular regions of the spinal column to control pain, the modulation may in some instances be directed to other neurological structures and/or target neural populations of the spinal cord and/or other neurological tissues. Some embodiments can have configurations, components and/or procedures different than those described in this section, and other embodiments may eliminate particular components or procedures. A person of ordinary skill in the relevant art, therefore, will understand that the present disclosure may include other embodiments with additional elements, and/or may include other embodiments without several of the features shown and described below with reference to FIGS. 1A-8.

In general terms, aspects of many of the following embodiments are directed to producing a therapeutic effect that includes pain reduction in the patient. The therapeutic effect can be produced by inhibiting, suppressing, down-regulating, blocking, preventing, or otherwise modulating the activity of the affected neural population, referred to generically herein as "stimulation" or "modulation". In many embodiments of the presently disclosed techniques, therapy-induced paresthesia is not a prerequisite to achieving pain reduction, unlike standard SCS techniques. It is expected that the techniques described below with reference to FIGS. 1A-8 can produce more effective, more robust, less complicated and/or otherwise more desirable results than can existing spinal cord stimulation therapies.

Many embodiments of the technology described below may take the form of computer-executable instructions, including routines executed by a programmable computer and/or controller. Those skilled in the relevant art will appreciate that the technology can be practiced on computer systems other than those shown and described below. The technology can be embodied in a special-purpose computer or data processor that is specifically programmed, configured or constructed to perform one or more of the computer-executable instructions described below. Accordingly, the terms "computer" and "controller" as generally used herein refer to any data processor and can include Internet appliances and hand-held devices (including palm-top computers, tablet computers, wearable computers, cellular or mobile phones, multi-processor systems, processor-based and/or programmable consumer electronics, network computers, mini computers and the like). Information handled by these computers can be presented at any suitable display medium, including a CRT display or LCD.

The technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on computer-readable media, including magnetic or optically readable or removable computer disks, as well as distributed electronically over networks. Data structures and transmissions of data particular to aspects of the technology are also encompassed within the scope of particular embodiments of the disclosed technology.

FIG. 1A schematically illustrates a representative patient system 100 for providing relief from chronic pain and/or other conditions, arranged relative to the general anatomy of a patient's spinal cord 191. The overall patient system 100 can include one or more signal delivery devices 110, which may be implanted within a patient 190, typically at or near the patient's spinal cord midline 189, coupled to an implantable signal (e.g., pulse) generator 101. The signal delivery devices 110 carry features for delivering therapy to the patient 190 after implantation. The signal generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or lead body or bodies 111 (identified individually as a first lead 111a and a second lead 111b). As used herein, the terms "lead" and "lead body" include any of a number of suitable substrates and/or support members that carry devices for providing therapy signals to the patient 190. For example, the lead or leads 111 can include one or more electrodes or electrical contacts that direct electrical signals into the patient's tissue, such as to provide for patient pain relief. In other embodiments, the signal delivery devices 110 can include structures other than a lead body (e.g., a paddle) that also direct electrical signals and/or other types of signals to the patient 190.

The signal generator 101 can transmit therapy signals (e.g., electrical signals) to the signal delivery devices 110 that up-regulate (e.g., stimulate or excite) and/or down-regulate (e.g., block or suppress) target nerves. As used herein, and unless otherwise noted, to "modulate" or provide "modulation" to the target nerves refers generally to having either type of the foregoing effects on the target nerves. The signal generator 101 can include a machine-readable (e.g., computer-readable) medium containing instructions for generating and transmitting suitable therapy signals. The signal generator 101 and/or other elements of the system 100 can include one or more processor(s) 107, memory unit(s) 108 and/or input/output device(s) 112. Accordingly, the process of providing electrical signals, providing guidance information for positioning the signal delivery devices 110, and/or executing other associated functions can be performed by computer-executable instructions contained by computer-readable media located at the signal generator 101 and/or other system components. The signal generator 101 can include multiple portions, elements, and/or subsystems (e.g., for directing signals in accordance with multiple signal delivery parameters), carried in a single housing, as shown in FIG. 1A, or in multiple housings.

In some embodiments, the signal generator 101 can obtain power to generate the therapy signals from an external power source 103. The external power source 103 can transmit power to the implanted signal generator 101 using electromagnetic induction (e.g., RF signals). For example, the external power source 103 can include an external coil 104 that communicates with a corresponding internal coil (not shown) within the implantable signal generator 101. The external power source 103 can be portable for ease of use.

During at least some procedures, an external stimulator or trial modulator 105 can be coupled to the signal delivery devices 110 during an initial procedure, prior to implanting the signal generator 101. For example, a practitioner (e.g., a physician and/or a company representative) can use the trial modulator 105 to vary therapy parameters provided to the signal delivery devices 110 in real time, and select optimal or particularly efficacious parameters. These parameters can include the location from which the electrical signals are emitted, as well as the characteristics of the electrical signals provided to the signal delivery devices 110. In a typical process, the practitioner uses a cable assembly 120 to temporarily connect the trial modulator 105 to the signal delivery devices 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters, may not be performed.

The signal generator 101, the lead extension 102, the trial modulator 105 and/or the connector 122 can individually include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the signal generator 101, the trial modulator 105 and/or the connector 122. Receiving elements 109 can be at least generally similar in structure and function to those described in U.S. patent application Ser. No. 13/291,985, entitled MEDICAL DEVICE CONTACT ASSEMBLIES FOR USE WITH IMPLANTABLE LEADS, AND ASSOCIATED SYSTEMS AND METHODS, filed Nov. 8, 2011, which is incorporated by reference herein in its entirety. To the extent the foregoing application and/or any other materials conflict with the present disclosure, the present disclosure controls.

After a trial period with the trial modulator 105, the practitioner can implant the implantable signal generator 101 within the patient 190 for longer term treatment. The signal delivery parameters provided by the signal generator 101 can still be updated after the signal generator 101 is implanted, via a wireless practitioner's controller 117 (e.g., a laptop, remote, tablet, or other computing device used by the practitioner) and/or a wireless patient controller 106 (e.g., a patient's laptop, patient's remote, patient's smart phone, etc.).

In any of the foregoing embodiments, the parameters in accordance with which the signal generator 101 provides signals can be modulated during portions of the therapy regimen. For example, the frequency, amplitude, pulse width and/or signal delivery location can be modulated in accordance with a preset program, patient and/or physician inputs, and/or in a periodic, random, or pseudorandom manner. Such parameter variations can be used to address a number of potential clinical situations, including changes in the patient's perception of pain, changes in the preferred target neural population, and/or patient accommodation or habituation.

Certain aspects of the foregoing systems and methods may be simplified or eliminated in particular embodiments of the present disclosure. For example, in at least some instances, the therapeutic signals delivered by the system can produce an effect that is much less sensitive to lead location and signal delivery parameters (e.g., amplitude) than are conventional stimulation systems. Accordingly, as noted above, the trial and error process (or parts of this process) for identifying a suitable lead location and associated signal delivery parameters during the lead implant procedure can be eliminated. In addition to or in lieu of this simplification, the post-lead implant trial period can be eliminated. In addition to or in lieu of the foregoing simplifications, the process of selecting signal delivery parameters and administering the signals on a long-term basis can be significantly simplified. Further aspects of these and other expected beneficial results are discussed in greater detail below.

2.0 Representative Therapy Parameters

Nevro Corporation, the assignee of the present application, has conducted a multi-site clinical study during which multiple patients were first treated with conventional spinal cord stimulation (SCS) techniques, and then with newly developed techniques that are disclosed further below. This study was followed up by a further clinical study focusing on the newly developed techniques, which confirmed and expanded on results obtained during the initial study. Multiple embodiments of the newly developed techniques, therapies and/or systems are referred to as presently disclosed techniques, therapies, and/or systems, or more generally as presently disclosed technologies.

Figure 1B:
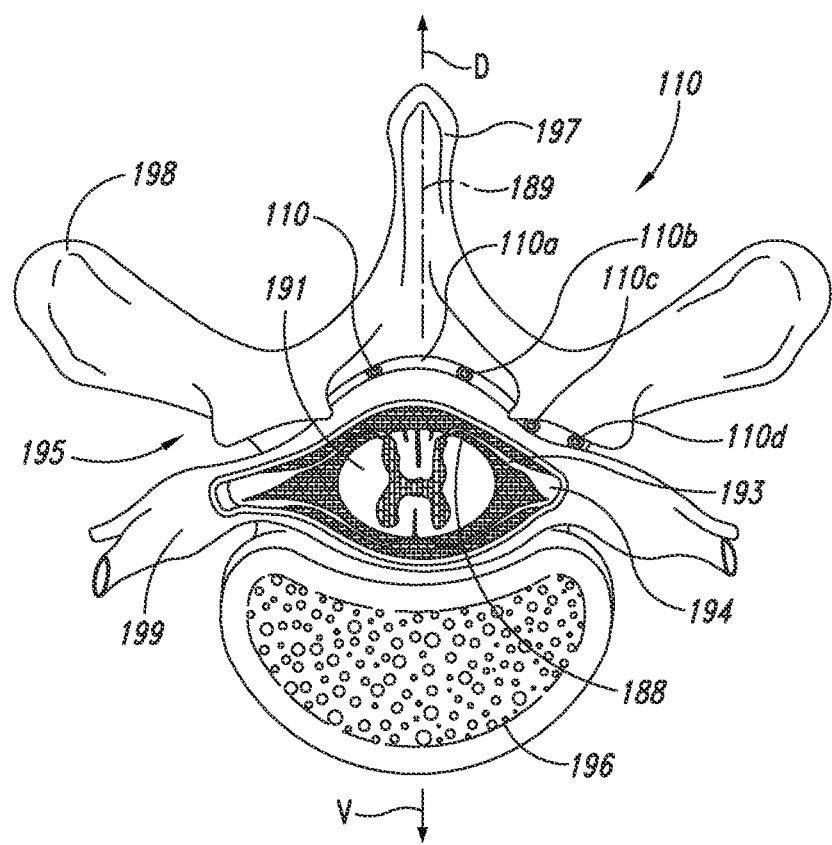
FIG. 1B is a partially schematic, cross-sectional illustration of a patient's spine, illustrating representative locations for implanted lead bodies in accordance with embodiments of the present disclosure.

Prior to the initial clinical study, selected patients were identified as suffering from primary chronic low back pain (e.g., neuropathic pain, and/or nociceptive pain, and/or other types of pain, depending upon the patient), either alone or in combination with pain affecting other areas, typically the patient's leg(s). In all cases, the low back pain was dominant. During the study, the patients were outfitted with two leads, each implanted in the spinal region in a manner generally similar to that shown in FIG. 1A. One lead was implanted on one side of the spinal cord midline 189, and the other lead was implanted on the other side of the spinal cord midline 189. FIG. 1B is a cross-sectional illustration of the spinal cord 191 and an adjacent vertebra 195 (based generally on information from Crossman and Neary, "Neuroanatomy," 1995 (published by Churchill Livingstone)), along with the locations at which leads 110 were implanted in a representative patient. The spinal cord 191 is situated between a ventrally located ventral body 196 and the dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the dorsal roots 193 and dorsal root ganglia 194. The leads 110 were positioned just off the spinal cord midline 189 (e.g., about 1 mm. offset) in opposing lateral directions so that the two leads 110 were spaced apart from each other by about 2 mm.

Patients with the leads 110 located as shown in FIG. 1B initially had the leads positioned at vertebral levels T7-T8. This location is typical for standard SCS treatment of low back pain because it has generally been the case that at lower (inferior) vertebral levels, standard SCS treatment produces undesirable side effects, and/or is less efficacious. Such side effects include unwanted muscle activation and/or pain. Once the leads 110 were implanted, the patients received standard SCS treatment for a period of five days. This treatment included stimulation at a frequency of less than 1500 Hz (e.g., 60-80 Hz), a pulse width of 100-200 µsec, and a duty cycle of 100%. The amplitude of the signal (e.g., the current amplitude) was varied from about 3 mA to about 10 mA. The amplitude was initially established during the implant procedure. The amplitude was then changed by the patient on an as-desired basis during the course of the study, as is typical for standard SCS therapies.

After the patient completed the standard SCS portion of the study, the patient then received modulation in accordance with the presently disclosed techniques. One aspect of these techniques included moving the leads 110 inferiorly, so as to be located at vertebral levels T9, T10, T11, and/or T12. After the leads 110 were repositioned, the patient received therapeutic signals at a frequency of from about 3 kHz to about 10 kHz. In particular cases, the therapy was applied at 8 kHz, 9 kHz or 10 kHz. These frequencies are significantly higher than the frequencies associated with standard SCS, and accordingly, modulation at these and other representative frequencies (e.g., from about 1.5 kHz to about 100 kHz) is occasionally referred to herein as high frequency modulation. The modulation was applied generally at a duty cycle of from about 50% to about 100%, with the modulation signal on for a period of from about 1 msec. to about 2 seconds, and off for a period of from about 1 msec. to about 1.5 seconds. The width of the applied pulses was about 30-35 µsec., and the amplitude generally varied from about 1 mA to about 4 mA (nominally about 2.5 mA). Modulation in accordance with the foregoing parameters was typically applied to the patients for a period of about four days during the initial clinical study.

U.S. patent application Ser. No. 13/831,539, incorporated by reference, illustrates and describes summaries of the clinical results obtained by testing patients in accordance with the foregoing parameters. In the clinical studies, patients were allowed choose from a limited number of signal modulation programs (e.g., two or three) each with a different amplitude and/or other signal delivery parameter, to address some or all of the patient's pain. In one such example, the patient activates one program before sleeping and another after waking. In another such example, the patient activates one program before sleeping, a second program after waking, and a third program before engaging in particular activities that would otherwise cause pain. This reduced set of patient options can greatly simplify the patient's ability to easily manage pain, without reducing (and in fact, increasing) the circumstances under which the therapy effectively addresses pain. In any embodiments that include multiple programs, the patient's workload can be further reduced by automatically detecting a change in patient circumstance, and automatically identifying and delivering the appropriate therapy regimen. Additional details of such techniques and associated systems are disclosed in co-pending U.S. application Ser. No. 12/703,683, incorporated herein by reference.

Another benefit observed during the clinical studies described above is that when the patient does experience a change in the therapy level, it is a gradual change. This is unlike typical changes associated with conventional SCS therapies. With conventional SCS therapies, if a patient changes position and/or changes an amplitude setting, the patient can experience a sudden onset of pain, often described by patients as unbearable. By contrast, patients in the clinical studies described above, when treated with the presently disclosed therapy, reported a gradual onset of pain when signal amplitude was increased beyond a threshold level, and/or when the patient changed position, with the pain described as gradually becoming uncomfortable. One patient described a sensation akin to a cramp coming on, but never fully developing. This significant difference in patient response to changes in signal delivery parameters can allow the patient to more freely change signal delivery parameters and/or posture when desired, without fear of creating an immediately painful effect.

3.0 Representative Medical Device Computing System

Figure 2:
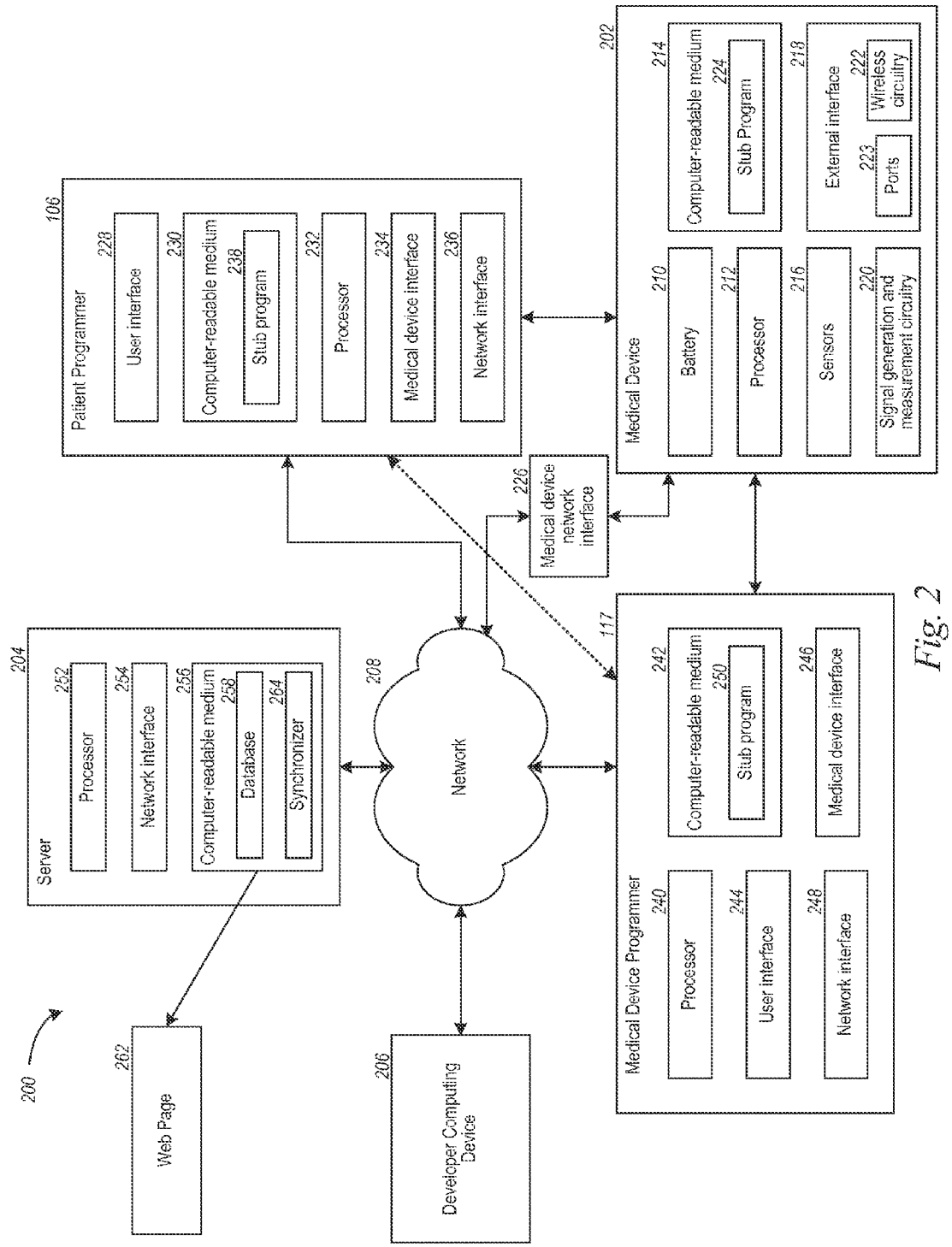
FIG. 2 is a schematic illustrating a representative medical device computing system including a spinal cord stimulation device.

FIG. 2 is a schematic illustration of a medical device computing system 200 configured in accordance with an embodiment of the present disclosure. The computing system 200 includes a medical device 202 that is communicatively coupled to the patient's controller 106 and the practitioner's controller 117. In a particular embodiment, the medical device 202 is the implanted signal generator 101 configured to deliver modulated signals to one or more signal delivery leads. The computing system 200 also includes a server 204 and a developer computing device 206 coupled, via a network 208, to one or more of the patient's controller 106, the practitioner's controller 117, and the medical device 202. Advantageously, the computing system 200 enables physicians to share modulation programs for medical devices 202 with other physicians. By sharing and receiving modulation programs that have been tested on multiple patients, individual physicians can initiate programs that have proven effective in other patients for symptoms that may be similar to those of the physician's particular patient. The computing system 200 can also provide the advantage of enabling remote access to one or more of the patient's controller 106, the practitioner's controller 117, and the medical device 202 from a remote location, e.g., via the network 208. Thus, in an emergency, the practitioner can remotely power down or reprogram the medical device 202 to suit an immediate need of the patient. Additional advantages of the computing system 200 can include enabling a developer to distribute firmware and/or software updates through the network 208, for example, to the patient's controller 106, the practitioner's controller 117, and/or the medical device 202. The developer's access to the controllers and medical device can be direct, through the network 208, or indirect, through the server 204, according to various embodiments.

The medical device 202 can be the signal generator 101 or the trial modulator 105, according to various embodiments of the present disclosure. The medical device 202 can include a battery 210, a processor 212, a computer-readable medium 214, sensors 216, and an external interface 218. The medical device 202 can also include signal generation and measurement circuitry 220.

The medical device 202 uses its various components to deliver modulation signals to the signal delivery device 110 (e.g., leads 111). The medical device 202 uses the processor 212 to read one or more programs from the computer-readable medium 214 to perform functions such as determine the orientation of the patient, determine the activity level of the patient, receive signal modulation programs from a practitioner's controller and/or patient's controller, execute the modulation programs, and monitor the characteristics of the signal delivery device 110 (e.g., impedance of the leads 111). For example, the medical device 202 can use the processor 212 to receive one or more programs via the ports 223 (e.g., USB ports) or the wireless circuitry 222 of the external interface 218. In some implementations, the wireless circuitry 222 enables the medical device 202 to communicate via one or more proprietary or standardized wireless standards, such as 802.11, Bluetooth, near field communications (NFC), or the like. The medical device 202 can also use the processor 212 to control the signal generation and measurement circuitry 220 to measure characteristics of the medical device 202, such as to measure voltage levels of the battery 210.

The medical device 202 may have one or more programs that enable the medical device 202 to receive firmware and software updates and/or upgrades via the external interface 218. For example, the computer readable medium 214 may include a stub program 224 which, when executed by the processor 212, can cause the medical device 202 establish a connection, request a firmware/software update, receive the update, and automatically install the update. The stub program 224 can cause the medical device 202 to request the update from the practitioner controller 117 (and/or the patient controller 106, in at least some embodiments) and/or from the server 204. Upon installation of the updated firmware and/or software, the medical device can use the external interface 218 and/or can use the stub program 224 to send an email, a text message, and/or other indication that firmware and/or software on the medical device 202 has been updated. In some embodiments, the stub program can send a message that causes the physician's controller or the patient's controller to display a message, such as, "firmware update 1.4 has been completed."

In some embodiments, the computing system 200 can include a medical device network interface 226. The medical device network interface 226 can operate as a communications conversion device for the medical device 202 to enable the medical device 202 to communicate directly with the network 208. The medical device network interface 226 can thereby enable the medical device 202 to communicate with the developer computing device 206, the server 204, and/or other computing devices directly via the network 208, in the absence of the patient's controller 106 and the practitioner's controller 117. At times, the medical device 202 may be configured so that the wireless circuitry 222 of the external interface 218 is limited to proprietary medical device communications protocols without being enabled to communicate via standard communication protocols such as Wi-Fi or Bluetooth. In these instances, the medical device network interface 226 may be configured to communicate over the proprietary medical device communications protocol that is the same as the proprietary medical device communication protocol implemented by the medical device 202. The medical device network interface 226 can also include wireless circuitry to detect and amplify weak wireless signals from the medical device 202, allowing the medical device 202 to transmit at low powers to extend battery life. In some embodiments of the present disclosure, the medical device network interface 226 includes a network card so a patient can connect the medical device network interface 226 to the patient's home or work network. Advantageously, the medical device network interface 226 can monitor the status of the patient, and/or the characteristics of the medical device 202, and may enable the medical device 202 to send alerts or to receive urgent updates to the patient's physician, to a manufacturer, to a developer, and/or to the patient via the network 208 and/or via the server 204.

The patient's controller 106 includes various components to enable the patient to power, program, and/or otherwise control the medical device 202, in accordance with embodiments of the present disclosure. The patient's controller 106 can include a user interface 228, a computer readable medium 230, a processor 232, a medical device interface 234, and a network interface 236. The user interface 228 can include physical buttons, switches, other physical inputs, or any number of indicators (e.g., light emitting diodes). The user interface 228 may also include a graphical user interface displayable on the patient's controller 106 via, for example, a display screen. The computer readable medium 230 can store one or more sets of instructions which, when executed by the processor 232, cause the patient's controller 106 to perform various functions. In some embodiments, the processor 232 causes the patient's controller 106 to perform various functions in response to inputs received from the patient via the user interface 228. The computer-readable medium 230 can also include instructions that cause the processor 232 to transmit one or more modulation programs from the patient's controller 106 to the medical device 202, e.g., with the medical device interface 234 and/or using the network interface 236.

In particular embodiments of the present disclosure, the computer readable medium 230 stores a limited number of predetermined programs (e.g., 3 programs) from which the patient may select from for programming the medical device 202. The patient's controller 106 may communicate directly with the practitioner's controller 117 to receive the programs using, for example, the medical device interface 234 or using the network interface 236.

By incorporating both a medical device interface 234 and a network interface 236, the patient's controller 106 can be used for generating alerts for the practitioner. For example, the patient's controller 106 can be configured to periodically query the medical device 202 for status updates for electrical characteristics of the leads 111, for the activity level or position of the patient. In response to receiving a status update from the medical device 202 that exceeds an upper threshold or a lower threshold, the patient's controller 106 can be configured to transmit one or more alerts via the network interface 236 to the server 204. Upon receipt of an alert, the server 204 can be configured to transmit the alert to the patient's physician and/or to a hotline or care center, such as one that is contracted to monitor the health of patients who are carrying medical devices 202.

The computer-readable medium 230 can include non-volatile memory for storing information received by the patient controller 106. For example, the computer-readable medium can be used to record the status of the patient and record the status of the medical device 202 for future analysis. The practitioner's controller 117, the developer computing device 206, and the server 204 are each examples of devices that may request the recorded information to enable practitioners, scientists and/or other suitable personnel to evaluate the recorded information. For example, the patient's controller 106 can record levels of discomfort using the user interface 228, and practitioners can analyze and graph the levels of discomfort to make improvements to the medical device 202 and/or the programs executed by the medical device 202.

The computer-readable medium 230 may also include a stub program 238 that is configured to automatically update firmware and/or software on the patient's controller 106. According to some embodiments of the present disclosure, the stub program 238 can automatically fetch and install firmware and/or software updates on the patient's controller 106. The stub program 238 receives the updates by: establishing a connection with another computing device (e.g., the practitioner's controller 117, the server 204, and/or the developer computing device 206); querying the computing device for firmware and/or software updates (e.g., USB driver updates, network interface updates, user interface updates, or the like); and automatically installing the updates. The stub program 238 can install the updates onto the patient programmer 106 and/or can be configured to install the updates onto the medical device 202. Additional representative embodiments of the patient's controller 106 will be described below in connection with subsequent Figures.

The practitioner's controller 117 can be communicatively coupled to the medical device 202 and/or the patient's controller 106 in order to distribute programs, upload recorded information, or to monitor the real-time status of the patient. In particular embodiments, the practitioner's controller 117 can be a desktop, laptop, and/or netbook computer that is configured to perform one or more of the various functions described hereafter. In other embodiments, the practitioner's controller 117 can be a tablet computing device or a smart phone having a medical device interface detachably coupled to it to enable wireless communications with the medical device 202. The practitioner's controller 117 can include a processor 240, a computer-readable medium 242, a user interface 244, a medical interface 246, and a network interface 248, in accordance with an embodiment of the present disclosure. The processor 240 can read and execute instructions for programs stored on the computer-readable medium 242. Execution of the instructions can cause the processor 240 to operate the user interface 244 and to communicate with the medical device 202, the patient's controller 106, the server 204, and/or the developer computing device 206. In accordance with various embodiments of the present disclosure, the practitioner's controller 117 can be configured to directly or indirectly communicate with the medical device 202 and/or the patient's controller 106 using one or more of the medical device interface 246 and the network interface 248.

The user interface 244 can include one or more physical and/or virtual buttons, slides, knobs, dials, touchscreens, or the like. The user interface 244 can be configured to receive defining parameters for modulation programs. The user interface 244, as will be discussed in more detail below, can be configured to display one, two, or more (e.g., all) modulation programs that have been defined by one or more physicians and that have been loaded onto the practitioner's controller 117. In some implementations, the user interface 244 enables a practitioner to access a repository of modulation signal programs stored on the server 204 and enables the practitioner to selectively download programs that have received positive feedback for treating symptoms similar to those experienced by the current patient. Various representative implementations of the user interface 244 and its corresponding sub-elements will be described in connection with subsequent FIGS. 7B-7Q.

The medical device interface 246 can be implemented using a variety of techniques, in accordance with embodiments of the present disclosure. In one example, the medical device interface 246 includes an antenna included within a PCMCIA card inserted into a port in a laptop or netbook. In another example, the medical device interface 246 may be attachable to a serial port, a parallel port, a USB port, a network port, a telephone jack, or another suitable port located in a desktop or laptop computer and may include variable lengths of wiring, an antenna, and/or other wireless communications interface element. In yet other embodiments, the medical device interface 246 includes a mini USB port, a micro-USB port, and/or any one of a number of proprietary ports connectable to a tablet or other computing device (e.g., Apple® computing device ports, and/or Apple® iPad® computing device ports). The medical device interface 246 may include one or more antennas and tuning circuitry useful for modulating signals at frequencies that are appropriate for communicating directly with the wireless circuitry 222 of the medical device 202. In some embodiments, the medical device interface 246 can be a module that couples to a smart phone to enable a smart phone or personal digital assistant to operate as the practitioner's controller 117.

The computer readable medium 242 can include a stub program 250 that is configured to automatically retrieve and/or install updates to firmware and/or software. In a particular embodiment, the stub program 250 can retrieve and install firmware and/or software updates to improve interfacing with or programming the medical device 202 and/or the patient's controller 106. The stub program 250 can include instructions which, when executed by the processor 240, can cause the processor to establish a connection with and query one or more of the server 204 and the developer computing device 206 for updates related to the practitioner's controller 117. In some implementations, the stub program 250 includes instructions that cause the processor 242 to notify the practitioner and/or other user via the user interface 244 that a firmware and/or software update is available for the practitioner's controller 117. The stub program 250 may include instructions that prohibit the processor 240 from automatically installing and/or updating the firmware and/or software on the practitioner's controller 117 until the practitioner or other user has provided authorization for such an update, e.g., via the user interface 244. In some implementations, the authorization receivable via the user interface 244 is a predetermined password or pass code, a user-specified password or pass code, a biometric reading, a visual input, an audio input, or any combination of the foregoing, to protect the practitioner's controller 117 from unauthorized alteration or modification. Additional details regarding the practitioner's controller 117 and the user interface 244 will be provided below in connection with subsequent figures.

The server 204 can be configured as a repository for modulation signal programs and data recorded by individual medical devices 202. The server 204 can receive programs and program efficacy ratings from any practitioner's controller 117 in use to treat patients. Individual programs can include metadata (e.g., type of medical device, patient height, patient weight, patient symptoms), about the program to facilitate searches of the server 204. The server 204 can accumulate these programs and make the programs accessible to the practitioner's controllers 117 to allow practitioners to define programs for the medical devices 202 based on large sets of data. The server 204 may include a processor 252, a network interface 254, and a computer-readable medium 256. The server 204 can use the network interface 254 to communicate with one or more of the developer computing device 206, the patient's controller 106, the practitioner's controller 117, and the medical device 202.

The computer-readable medium 256 can include instructions and/or programs to enable the server 204 to operate as a repository for modulation signal programs. For example the computer-readable medium can include non-volatile memory and volatile memory for storing and executing a database 258. The database 258 receives, stores, and organizes modulation signal programs for medical devices 202. Examples of modulation signal programs that are made available to the database 258 include programs that have been rated by patients and/or physicians for being effective for treating specific symptoms. For example, individual received programs can have an efficacy rating for a particular symptom or ailment, such as upper back pain, mid back pain, lower back pain, leg pain, or the like. Some of the received programs can have an efficacy rating for more than one ailment. The database 258 may store and organize programs by symptoms, age of patients, height and weight of patient, severity of pain, whether the patient has undergone surgery, or any variety of combinations of one or more of the foregoing data points or characteristics of the programs. As discussed above, these characteristics of the programs can be saved as metadata in a file along with the program. The server 204 can use the database 258 to collect and store patient and program information from a single practitioner's controller 117 that is associated with multiple medical devices 202. In other implementations, the server 204 can use the database 258 to collect and store modulation signal programs from multiple practitioners' controllers 117 that may be associated with medical professionals working from geographically independent locations. Advantageously, the server 204 can analyze and organize the received programs and provide recommendations to physicians based on a larger sample of data than may be available to an individual physician.

The server 204, via the network 208, enables a practitioner to query the database 258 for modulation signal program recommendations. Because the database can be configured to organize or sort accumulated programs based on characteristics (e.g. physical characteristics) and/or or symptoms of patients, a practitioner can query the database 258 with one or more characteristics of a particular patient, and the database 258 can return programs having efficacy ratings that have been determined to be effective for other patients having similar characteristics or symptoms as the patient of the query. In some embodiments, the database 258 can be configured to return the one or two programs having the highest rating and/or efficacy ranking for a particular set of characteristics and/or symptoms. For example, the database may include sortable columns for characteristics of a patient such as physical characteristics (e.g., height, weight, age), characteristics related to their condition (e.g., location of injury, location of pain, intensity of pain, duration of pain), or other characteristics of the patient (e.g., whether or not the patient has undergone surgery, the activity level of the patient, and the position or orientation of the patient). To respond to a query, the database 258 may be configured to sort by the sum, average, and/or other mathematical characteristic of multiple columns of characteristics and/or symptoms to return the most relevant programs.

Individual programs received or stored in the database 258 may have an assigned rank. The rank assigned to individual signal modulation programs may reflect the relative effectiveness of a program to reduce pain and other symptoms in a patient who has a particular set of characteristics (e.g., age, height, weight, location of pain, etc.). The patient or practitioner may assign a rank for a program using the patient's controller 106, or the practitioner's controller 117, respectively. In particular embodiments of the present disclosure, the patient's controller 106, the practitioner's controller 117, and/or the medical device 202 automatically assigns and/or associates an efficacy rank to individual modulation signal programs based on feedback and/or input received from the patient, changes in activity level of the patient (e.g., as detected and/or determined by sensors carried by the medical device 202), or based on reports of decreases in pain medication prescribed for the patient or self-reported by the patient. In some implementations, a physician assigns an efficacy rating to individual modulation signal programs based on the physician's own observations of objective characteristics of the patient, e.g., reductions in pain reports, increases in flexibility, increases in mobility, and/or increases in stamina. In other embodiments, the efficacy rating may be determined by changes in the mobility of the patient as measured by sensors carried by the mobile medical device 202.

The server 204 may be configured to assign an efficacy rating to signal modulation programs that have not yet received an efficacy rating. The server 204 may periodically receive data from the medical device 202 via the patient's controller 106, the practitioner's controller 117, and/or the medical device network interface 226. The server 204 may store and analyze the received data. The server 204 may be configured to determine the efficacy of a program by correlating increases and decreases of patient mobility with modulation signal programs in use at the time of the changes in patient mobility. The server 204 can then assign higher ranks to signal modulation programs that correspond to greater reports of patient mobility and may assign lower ranks to signal modulation programs that are associated with less mobility for the patient. Of course, the server 204 can be configured to account for expected times of decreased mobility, such as during rest, nap, and/or sleep times.

Some organizations may control and selectively share the information stored in the database 258. For example, a hospital may operate the server 204 and only provide access to the database 258 to physicians affiliated with or working for the hospital. Thus, the server 204 may be used to collect, store, sort, and/or organize modulation programs for patients that pay for the services of the hospital. The hospital, or other organization, may selectively provide access to the database 258 as a paid-for service to other physicians or organizations, who are not affiliated with the hospital.

Some organizations may control the server 204 to provide a paid-for service of providing a modulation signal program repository to multiple groups or organizations. For example, an organization may enable subscribers, such as hospitals, medical groups, or individual physicians, to pay for access to the rankings of modulation signal programs as part of the subscription agreement. The organization controlling the server 204 may request or require subscribers to enable the server 204 to mine or receive subscriber rankings of individual modulation signal programs to increase the data set or sample size of programs stored by the database 258.

The server 204 may utilize a synchronizer 264 as a gateway between the server 204 and other computing devices to facilitate collection of medical device information. For example, the synchronizer 206 may be a collection of one or more programs configured to collect data from the patient's controller 106, the practitioner's controller 117, and/or the medical device 202. The synchronizer 264 may perform or may provide collection services as an intermediary between source devices and the database 258. After collecting data related to the medical device 202, synchronizer 264 may be configured to automatically insert the collected data into the database 258. In some implementations, the synchronizer 264 is installed and/or operated on a server that is independent of the server 204 that hosts the database 258. The synchronizer 264 may also be configured to push updates down to the source devices in response to "handshaking" or requests from one or more of stub programs 224, 238, and 250. In some implementations, the synchronizer 264 automatically distributes firmware and/or software updates to one or more of the patient's controller 106, the practitioner's controller 117, and a medical device 202 in response to receipt of such updates from a developer.

The computer-readable medium 256 can include instructions and/or programs to enable the server 204 to receive, generate, and/or distribute alerts or notifications. The alerts or notifications can be based on information received from the medical device 202. For example, if the medical device 202 detects that a physiological or biological attribute of the patient exceeds one or more thresholds, the medical device 202 may be configured to generate an alert and transmit the alert to the server 204 via the patient's controller 106, the practitioner's controller 117, or the medical device network interface 226. The server 204, in response to receipt of an alert from the medical device 202, may be configured to identify the patient associated with the medical device 202, identify the physician or healthcare provider associated with the patient, and transmit a text message, an email, a multimedia message, a telephone call, voicemail, and/or other suitable communication to the medical provider. In some particular embodiments of the present disclosure, the server 204 uses the synchronizer 264 to periodically collect or receive patient data associated with the medical device 202 and generate an alert or notification based on trends and/or patterns associated with the received data. Thus, the server 204 may be configured to receive alerts and redistribute alerts, and/or the server 204 may be configured to analyze data from the medical device 202 in order to generate notifications and alerts for distribution to the patient and/or the medical professional associated with the patient.

The computer-readable medium 256 can include instructions or programs to enable the server 204 to host a webpage 262. The webpage 262 can allow patients and/or practitioners to review data collected by the medical device 202, to submit feedback regarding the efficacy of one or more programs, or to remotely power down or otherwise alter the programs stored on the medical device 202.

The developer computing device 206 may be communicatively coupled to one or more of the patient's controller 106, the practitioner's controller 117, the medical device 202, and the server 204 to provide or implement remote firmware and/or software updates. The developer computing device 206 may be any one of a variety of computing devices for enabling the developer to view the status of the medical devices, and/or write, test, debug, execute, and/or simulate code, depending upon the embodiment. The developer computing device 206 may be a desktop computer, server, a laptop, net book, a notebook, a personal digital assistant, a smart phone, a tablet computer, or other device capable of communicating over a network.

The computing system 200 includes various components that may enable patients and physicians to receive automated firmware and/or software updates, to provide and receive ranked modulation signal programs, to receive and/or generate alerts, or provide other remote services.

4.0 Representative Methods of Operating the Computing System

Figure 3A:
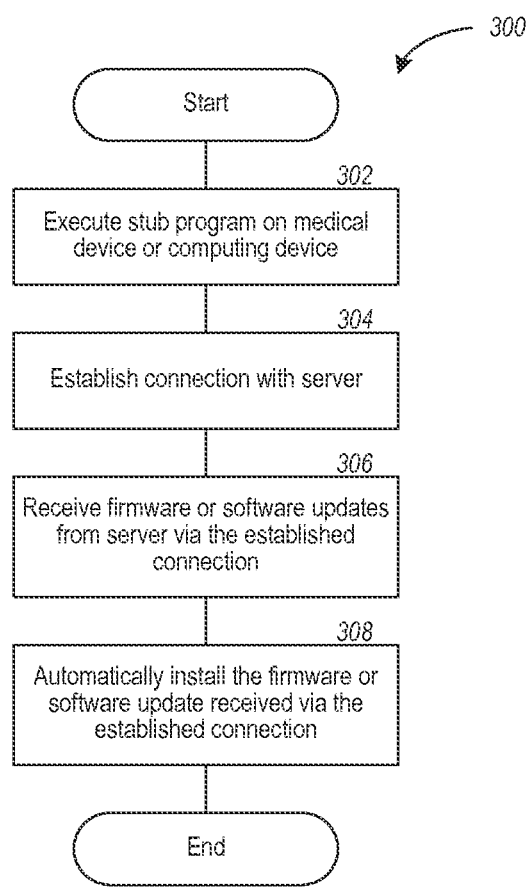
FIGS. 3A-3C are flow diagrams illustrating methods of operating the computing system of FIG. 2 in accordance with particular embodiments of the present disclosure.
Figure 3B:
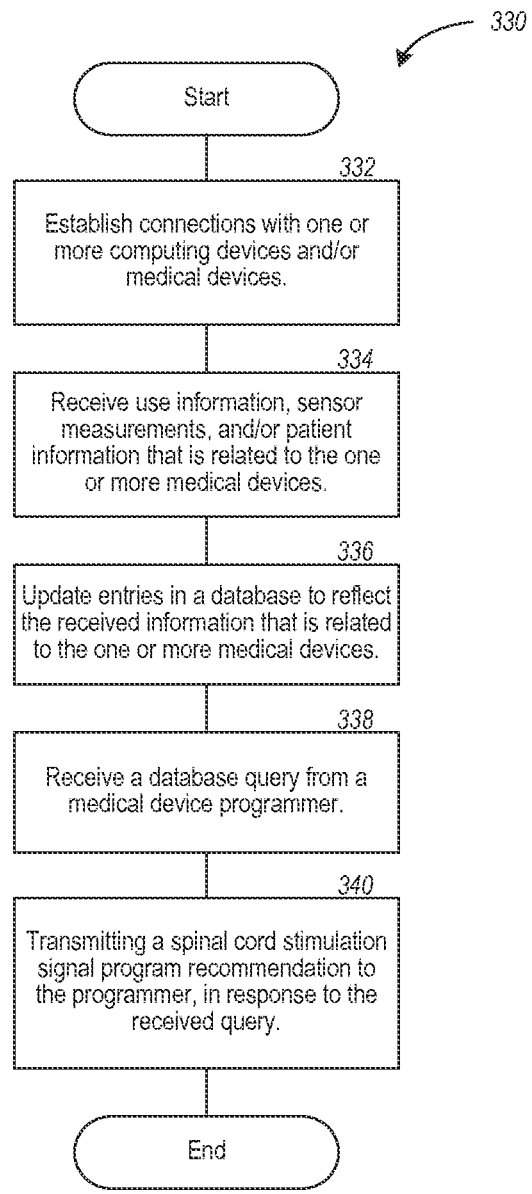
Figure 3C:
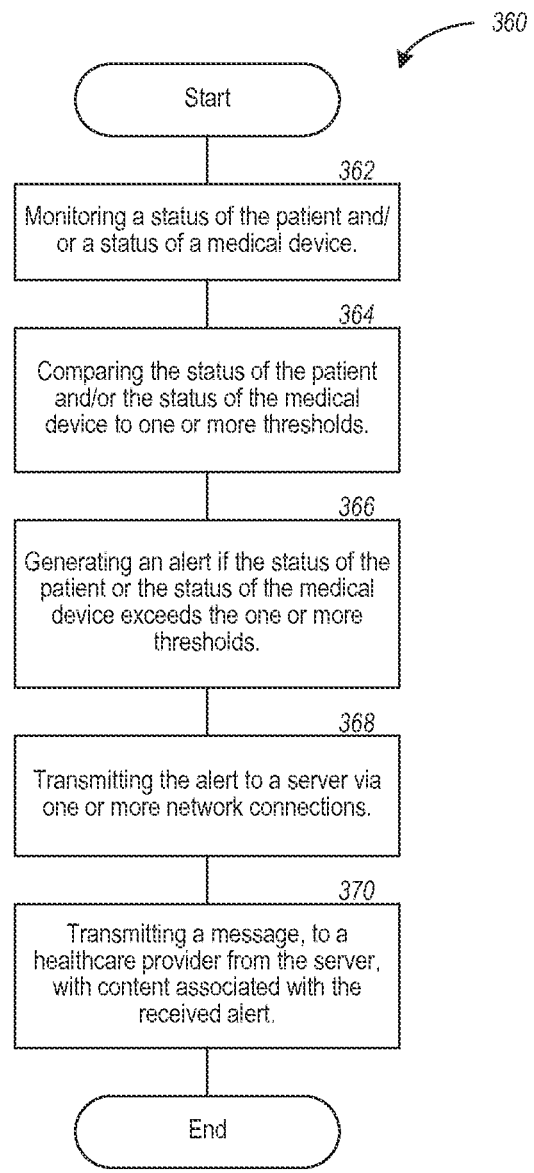

FIGS. 3A-3C illustrate flow diagrams of representative methods of operating various portions of the computing system 200.

FIG. 3A is a flow diagram of a representative method 300 for automatically updating computing devices within the computing system 200, in accordance with an embodiment of the present disclosure. At block 302, a medical device or computing device executes a stub program to facilitate automatically updating the medical device or the computing device. The medical device or the computing device can execute the stub program (e.g., the stub programs 224, 238, 250 referred to in FIG. 2) at different time intervals. For example, the computing device can execute the stub program periodically, whenever a network connection is established, each time the computing device or the medical device is booted or restarted, or based on other predetermined events. Examples of medical devices or computing devices that may execute a stub program include the patient's controller 106, the practitioner's controller 117, and the medical device 202 (referred to in FIGS. 1 and 2). At block 304, the medical device or the computing device establishes a connection with a server e.g., server 204 referred to in FIG. 2. The patient's controller 106, the practitioner's controller 117, or the medical device 202 may establish a connection with the server 204 via the network 208 using one or more network interfaces (e.g., network interfaces 236, 248, 226 referred to in FIG. 2). Once connected, the stub program may cause the medical device or the computing device to query the server for updates or otherwise determine if firmware and/or software updates are available for the medical device or the computing device. At block 306, medical device or the computing device receives firmware and/or software updates from the server via the established connection. At block 308, the stub program causes the medical device or the computing device to automatically install the firmware and/or software update received from the server via the established connection. If needed, the medical device or the computing device may recycle power on the device to complete full installation of the received update, in accordance with a particular embodiment of the present disclosure.

FIG. 3B is a flow diagram of a representative method 330 for synchronizing a server with multiple computing devices within the computing system 200, in accordance with an embodiment of the present disclosure. In one particular representative embodiment, the server can be configured to receive data from various computing devices or medical devices and can be configured to distribute or push information to one or more computing devices in response to a query from the one or more computing devices.

At block 332, the server establishes network connections with one or more computing devices and/or medical devices. Examples of the computing devices include the patient's controller 106, the practitioner's controller 117, and the medical device 202.

At block 334, the server receives information associated with the use of a medical device, sensor measurements, and/or patient information that is related to the one or more medical devices. For example, the server can receive information describing which modulation signal programs have been executed by a medical device, the duration for which the programs were executed, the times and durations the medical device was switched off. Examples of sensor information the server may receive includes voltage and/or current measurements of a battery within medical device, impedance measurements of the signal delivery devices (e.g., the impedance between electrodes of a lead 111), and the like. The server can be configured to request such information from patient controllers, practitioner controllers, and/or medical devices. Alternatively, these devices can be configured to automatically transmit information associated with the patient and/or the medical device to the server without initially receiving a request from the server.

At block 336 the server updates a database with the information received from the one or more medical devices. The database can, for example, include various characteristics of patients and can correlate patient characteristics with efficacy of one or more programs. For example, the server can receive modulation programs that are ranked by patients and/or practitioners and can correlate program efficacy with characteristics of pain of the patient, such as by the location, intensity, and/or intensity of the pain.

At block 338, the server receives a database query from a medical device programmer, such as the practitioner's controller 117. The request can be submitted by a medical health provider using a query interface hosted by the practitioner's controller 117, or by using a query interface that is hosted by the server 204, e.g., the webpage 262.

At block 340, the server transmits a modulation program recommendation to the healthcare provider or the practitioner's controller, in response to the received database query. The recommendation can be used by the healthcare provider to program the medical device and/or the patient's controller for delivery of therapy to the patient. According to various embodiments of the method 330, the server can use a synchronizer module or synchronizer program, such as the synchronizer 264, to execute one or more of the procedures of the blocks 332-340.

FIG. 3C is a flow diagram of a representative method 360 of providing alerts to a healthcare provider using the computing system 200. Providing alerts can include transmitting a text message, a short message service ("SMS") message, a multimedia messaging service ("MMS") message, an email, a voicemail, a page, and/or other message to a healthcare provider from the server with content associated with the alert.

At block 362, a patient's controller, a practitioner's controller, and/or a medical device monitors the status of a patient and/or a status of a medical device. The status of the patient can include the body position of the patient. Examples of the status of the medical device can include voltage level of the battery, whether the device is powered on/off, or the like. In some embodiments, the patient's controller or the medical device can be configured to associate electrical characteristics of the medical device, or measurements from sensors carried by the medical device, with a status of the patient, e.g. whether the patient is experiencing pain, discomfort, sensory effects, and/or other side effects.

At block 364, a computing device or medical device compares the status of the patient or the status of the medical device to one or more thresholds.

At block 366, the computing device or the medical device generates an alert if one or more of the statuses exceed one or more thresholds. For example, if the battery voltage is low, the medical device or the patient's controller may determine that the patient should charge the battery.

At block 368, the patient's controller or medical device transmits the alert to a server, e.g., server 204, via one or more network connections.

At block 370, the server transmits a message to the patient or to a healthcare provider with content associated with the received alert. The server can receive the alert in a format of a first communication protocol, e.g., HTTP, can convert the alert into a format of a second communication protocol, and can transmit the alert via the second format or the second communication protocol, e.g., SMS message, text message, email, or the like. As disclosed above in connection with FIG. 2 and computing system 200, upon receipt of an alert, the practitioner can use the webpage 262, the practitioner's controller 117, or similar tool to remotely access the medical device 202 via the network 208 in order to remotely modify programming or operation of the medical device 202.

5.0 Representative Programmer Configurations

The robust characteristics of the presently disclosed therapy techniques may enable other aspects of the overall system described above with reference to FIGS. 1A-B to be simplified. For example, the patient's controller and the practitioner's controller can be simplified significantly because the need to change signal delivery parameters can be reduced significantly or eliminated entirely, in accordance with some embodiments of the present disclosure. In particular, it is expected that in certain embodiments, once the lead is implanted, the patient can receive effective therapy while assuming a wide range of positions and engaging in a wide range of activities, without having to change the signal amplitude and/or other signal delivery parameters. As a result, the patient's controller need not include any programming functions, but can instead include a simple on/off function (e.g., an on/off button or switch). The patient's controller may also include an indicator (e.g., a light) that identifies when the signal generator is active. This feature may be particularly useful in connection with the presently disclosed therapies because the patient will typically not feel paresthesia, unless the system is configured and programmed to deliberately produce paresthesia in addition to or in lieu of the therapy signal. In particular embodiments, the practitioner's controller can be simplified in a similar manner, though in some cases, it may be desirable to maintain at least some level of programming ability at the practitioner's controller. Such a capability can allow the physician to select different contacts and/or other signal delivery parameters in the rare instances when the lead migrates or when the patient undergoes physiological changes (e.g., scarring) or lifestyle changes (e.g., new activities) that are so significant they require a change in the active contact(s) and/or other signal delivery parameters. FIGS. 4A-8 illustrate representative devices and associated methodologies that reflect one or more of the foregoing features in accordance with particular embodiments of the present disclosure.

FIG. 4A is a partially schematic illustration of a remote control device 400 (e.g., a patient's controller) configured in accordance with an embodiment of the present disclosure. The patient's controller 400 can be operated by a patient during the course of therapy, e.g., generally as described above with reference to FIGS. 1-3C. In a particular embodiment shown in FIG. 4A, the patient's controller 400 includes a wireless transmitter and the user interface is a single input device 401. The wireless transmitter establishes a communication link 405 with an implanted signal generator (e.g., the signal generator 101 described above with reference to FIGS. 1A and 2). A link indicator 403 indicates whether the patient's controller 400 has established the communication link 405 with the signal generator, which in turn enables directive signals provided by the input device 401 to be transmitted to the signal generator.

In a further particular aspect of this embodiment, the single input device 401 controls only two states of the associated implanted signal generator. For example, the input device 401 can control only whether the signal generator is "on" (e.g., enabled to provide modulating signals to the patient) or "off" (e.g., disabled from providing modulating signals to the patient). In yet a further particular embodiment, the single input device 401 can be limited so as to (a) allow the signal generator to be on so long as the input device 401 is not activated, and to (b) shut the signal generator down if the input device 401 is activated. In this embodiment, the practitioner initially activates the signal generator, and the patient can shut it off (e.g., under specific conditions, such as an emergency). The practitioner's input is then required to re-activate the signal generator. A power indicator 402 (e.g., an LED or other visual indicator, audio indicator, or other type of indicator) identifies whether the input device 401 has placed the associated signal generator in an on state or an off state. This feedback feature may be of particular value to a patient receiving non-paresthesia-inducing therapy, because the patient may not immediately sense such therapy otherwise. The input device 401 can include a push button, touch pad, or other suitable component. In a particular embodiment, the input device 401 can send a different directive signal to the signal generator, depending upon whether the input signal is intended to turn the signal generator on or off. In another embodiment, the input device 401 can send the same signal to the signal generator, and the signal generator simply toggles between an on state and an off state with each new input received via the input device 401. In any of these embodiments, the patient's controller 401 can be sized and shaped to be easily held and operated with one hand.

FIG. 4B is a partially schematic illustration of a patient's controller 400 configured in accordance with another embodiment of the present disclosure. In this embodiment, the input device 401 can direct the associated implanted signal generator to be in one of, at most, three or possibly more (e.g., four) alternate states. For example, the implanted signal generator can be configured to deliver signals to the patient in accordance with, at most, three different signal delivery programs. By activating the input device 401, the patient can toggle between a first program, a second program, and a third program. Individual programs can have associated with it a corresponding program indicator 404a, 404b, 404c and the active program can be indicated by a different appearance of the corresponding indicator. For example, the program indicators 404a, 404b, and 404c can include lights, LEDs or other devices that are active (e.g., illuminated) when the associated program is active, and inactive when the associated program is inactive. In representative embodiments, the three programs can be sleep/awake/active programs or low/medium/high activity patient programs. In these and other embodiments, the difference between programs can be limited to current amplitude differences (as opposed to other differences, e.g., frequency differences and active contact differences). The patient's controller 400 can also be used to control whether the implanted signal generator is on or off, with an off state indicated when neither program indicator 404a, 404b, nor 404c is active. As discussed above with reference to FIG. 4A, the patient's controller 400 can issue different directive signals depending upon the desired target state at the implanted signal generator, or the patient's controller 400 can direct the same signal to the implanted signal generator, and the implanted signal generator can sequentially step through the states (e.g., off, program 1, program 2, program 3, off, etc.) with the arrival of individual new directive signal.

Figure 4C:
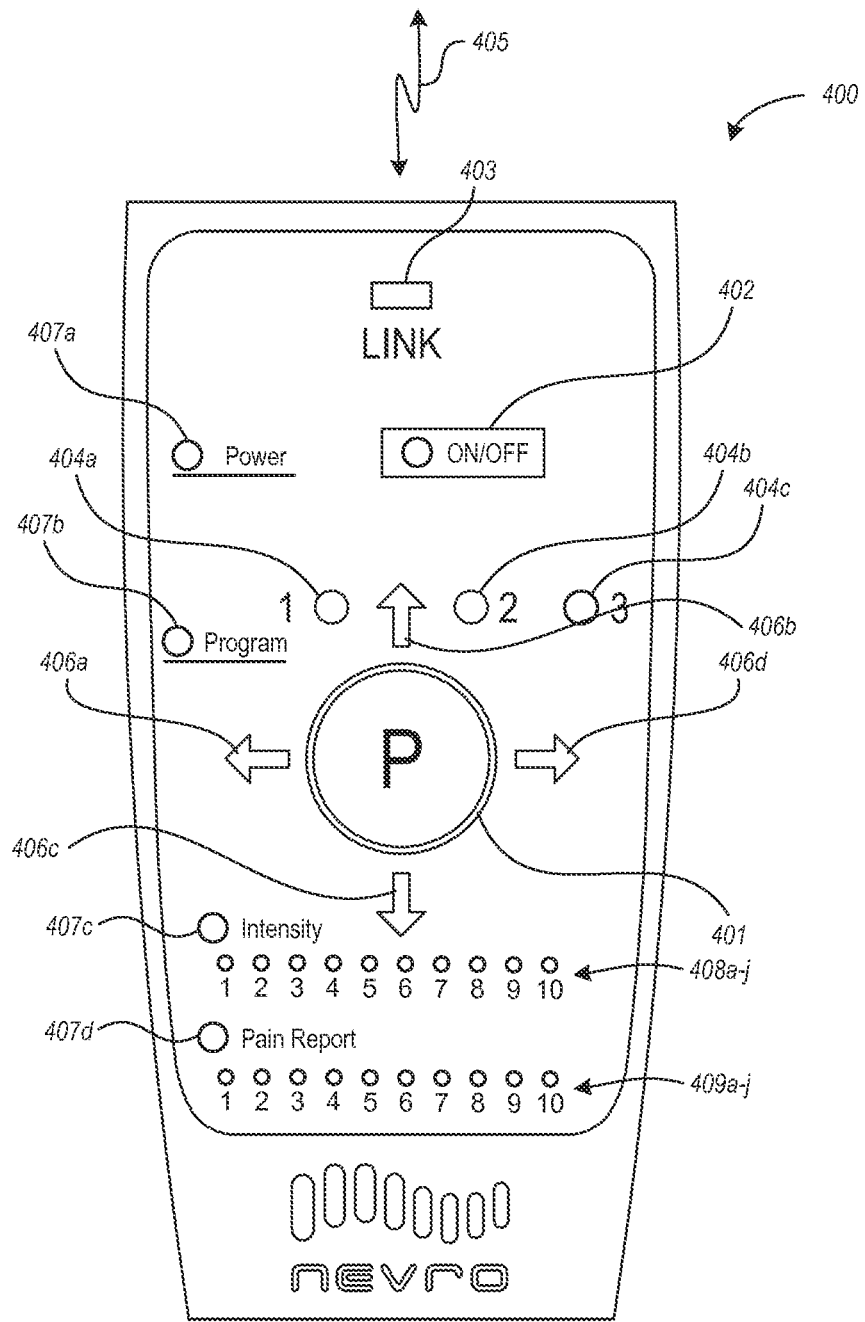

FIG. 4C is a partially schematic illustration of a patient's controller 400 configured in accordance with another embodiment of the present disclosure. In this embodiment, the input device 401 can be a multi-function button used to toggle and select between various power modes, programs, and parameters. For example, the input device 401 can be configured to be pressed up and down in the direction of arrows 406b and 406c to toggle between any of the indicators 407 (identified individually as indicators 407a-407d). Toggling between the indicators 407 can indicate that the remote is switching from one to another of a power mode, a programmer mode, an intensity mode, and a pain report mode. Individual ones of the indicators 407a-d can be configured to illuminate as the input device 401 is used to toggle or switch between the modes associated with individual respective indicators. The input device 401 can also be configured to be pressed left and right in the directions of arrows 406a and 406b to facilitate detailed manipulation of each of the indicated modes. For example, if the input device 401 is pressed down in the direction of the arrow 406c until the intensity mode indicator 407c is illuminated, the input device 401 can be pressed left and right to vary the amplitude or intensity of the signal modulation program being executed by the signal generator 101. In one particular embodiment, the input device 401 can be pressed in the middle to confirm and execute changes made to a particular mode. In response to a change made to a particular mode, the patient's controller 400 can send a directive signal to the implanted signal generator to cause the implanted signal generator to modify its operation. As discussed above, although the input device 401 is depicted herein as a button or a multifunction button, other embodiments such as a mouse ball or touchscreen are also encompassed within the scope of this present disclosure.

The patient's controller 400 represented in FIG. 4C can include an intensity mode and a pain report mode to enable the patient to fine tune the patient's therapy with greater granularity than the embodiments of the patient's controller 400 illustrated in FIGS. 4A and 4B. For example, the intensity mode may include a mode selection indicator 407c and ten indicators 408a-j labeled from '1' to '10' to enable the patient to visually identify and change the intensity or amplitude with which modulation signals are delivered by the signal generator 101. Although ten indicators are illustrated, more or fewer indicators may be used with similar or different labels (e.g., 'low', 'medium', 'high').

The pain report mode can include a mode selection indicator 407d and ten indicators 409a-j labeled from '1' to '10' to enable the patient to visually identify and report a level of pain experienced during a particular program. Data associated with the pain report mode can be stored on the patient's controller 400, can be transmitted and stored in the implanted signal generator 101, or can be distributed by a network to other computing devices (e.g., practitioner's controller 117 or server 204). The data associated with the pain report mode can then be used to rate, rank, or otherwise label the efficacy of a particular program and its associated parameters.

One feature of the embodiments described above with reference to FIGS. 4A, 4B, and 4C is that the patient's controller 400 can include a limited function input device 401, e.g., an input device that is prohibited from carrying out certain actions. In particular, the patient's controller 400 shown in FIG. 4A can only change the state of the corresponding implanted signal generator between an on state and an off state, and the patient's controller 400 shown in FIG. 4B can only change the state of the corresponding implanted signal generator between an off state, a first program, a second program, and a third program. Notably, the patient's controller 400 shown in FIG. 4A does not have control over the amplitude, frequency, and/or other signal delivery parameters in accordance with which the modulating signal is provided to the patient. The patient's controller 400 shown in FIG. 4B has limited control over these features, in that the different programs will typically include different signal delivery parameters. The patient's controller 400 shown in FIG. 4C can have control over the amplitude of any program selected but not over the frequency and/or other signal delivery parameters. However, the patient's controller absolute control of the amplitude can be restricted or confined by boundaries or hard-stops set by the practitioner. Such features will be discussed below in connection with the interface for the practitioner's controller.

One advantage of the foregoing arrangement is that it can simplify the patient's life by reducing the patient's involvement with controlling the therapy provided by the electrical signals. In this embodiment, reduced control is not a disadvantage for the patient, but instead capitalizes on the robust nature of the therapy described above. For example, the robust nature of the therapy can reduce or eliminate the need for the patient to control signal amplitude, delivery location and/or other parameters without impacting the efficacy of the therapy. Another advantage associated with the foregoing features is that the practitioner can more easily track the therapy delivered to the patient. For example, the patient's controller 400 can store information identifying when the implanted signal generator is activated and, if the patient has enabled multiple programs, which program is active. With fewer variables to control, the data are expected to be simpler to understand and easier to make use of.

In other embodiments, the overall system can operate in other manners to achieve at least some of the foregoing results. For example, the signal generator can be configured to respond only to certain requests, or not respond to particular requests from a patient's controller. In a particular example, the signal generator can be configured to not respond to requests from a patient's controller for a change in amplitude, program, or active contact selection. One application for this approach is that it allows existing patient controllers to be used in the limited-function manner described above for the patient's controller 400 of FIG. 4A.

The patient's controller 400 can be manufactured with different models having unique sets of features. For example, a first model of the patient's controller 400 can be manufactured to include the feature set of the patient's controller 400 of FIG. 4A, a second model of the patient's controller 400 can be manufactured to include the feature set of the patient's controller 400 of FIG. 4B, and a third model of the patient's controller 400 can be manufactured to include the feature set of the patient's controller 400 of FIG. 4C. With multiple models of patient's controllers 400 to choose from, a physician could assign or issue a first model, a second model, or a third model of the patient's controller 400 to a patient in accordance with the lifestyle, technological familiarity, or other needs of the patient.

Figure 5:
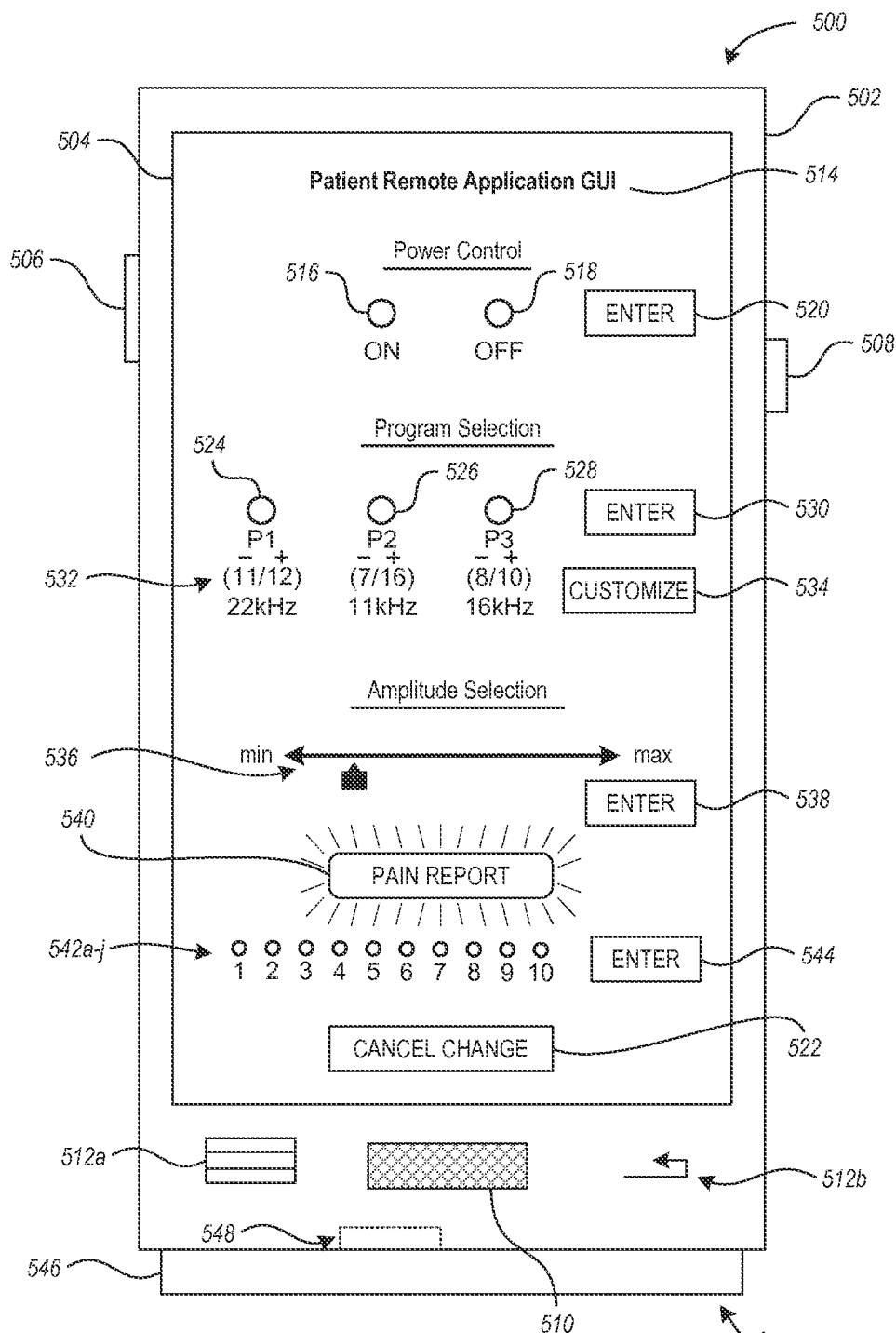
FIG. 5 is a schematic illustrating a mobile device displaying a graphical user interface for a patient-operated controller in accordance with an embodiment of the present disclosure.

FIG. 5 is a representative partial schematic illustration of a mobile device displaying a graphical user interface of a patient's controller application, in accordance with an embodiment of the present disclosure. By distributing and executing a patient's controller application for use on pre-existing consumer electronics, patients who have smart phones or other application-compatible mobile devices may benefit from being able to use a device that the patient already owns and is accustomed to carrying with them. The patient's controller application can also provide the advantage of leveraging other features of consumer electronics, such as mobile access to data networks.

The mobile device 500 represents an example implementation of the patient's controller 106 illustrated in FIGS. 1A and 2. The mobile device 500 can include a housing 502, a display 504, a volume rocker button 506, a power button 508, a home button 510, and one or more menu buttons 512 (inclusive of menu buttons 512A and 512B). As described in connection with FIG. 2, the mobile device 500 can also include one or more processors, one or more computer-readable media for storing and executing the patient's controller application, and one or more wire-based or wireless network interfaces (some not shown in FIG. 5). Individual ones of the volume button 506, the home button 510, and the menu buttons 512 can be configured to control, select, or otherwise manipulate the patient's controller application GUI 514. In certain embodiments, however, the display 504 is a touch screen display configured to manipulate the patient's controller application graphical user interface ("GUI") 514. In particular, the display 504 can be configured to receive input from the user in response to sensing or detecting tactile input via a finger or object manipulated by the patient.

The patient's controller application GUI 514 includes several features that are similar to those described with respect to the patient's controller 400 of FIG. 4C. For example, the patient's controller application GUI 514 can include a power control feature, a program selection feature, an amplitude selection feature, and the pain report feature, among others. In response to receiving tactile inputs from the touch screen display 504 that correspond to one of the various features of the GUI 514, the mobile device 500 can be configured to process the input, save the settings or changes to settings selected by the user, transmit the received information to the server 204 via one or more network interfaces, and provide the patient's selections to the signal generator 101.

To enable a patient to control the power settings of the signal generator 101, the GUI 514 may provide an ON radio button 516, an OFF radio button 518, and an ENTER button 520. Using the radio buttons 516, 518, the patient may power up or power down the signal generator 101 by touching or hovering over one of the radio buttons 516, 518, and then by pressing the ENTER button 520. If the patient determines that he or she would prefer not to change the power setting of the signal generator 101, prior to pressing or manipulating the ENTER button 520, the user may press or manipulate the CANCEL CHANGE button 522.

The patient's controller application GUI 514 can enable a user to select or change between modulation programs by providing an input component for individual programs for the patient to select from. For example, a physician may prescribe three programs, e.g., P1, P2, and P3, to the patient and may authorize the prescribed number of programs for distribution to the patient's controller application. The patient's controller application may use the GUI 514 to display some or all of the programs, e.g., three, prescribed by the physician. Using an example of three programs, i.e., P1, P2, and P3, the GUI 514 may display, provide, or otherwise render radio button 524 for program P1, radio button 526 for program P2, and radio button 528 for program P3. Upon selection of one of the displayed programs, the user can select or press the ENTER button 530 to complete the selection or the user may press the CANCEL CHANGE button 522 to maintain the current or previous status of the application.

The GUI 514 can also display program information or program details 532 below or in proximity to the corresponding radio buttons 524, 526, 528. The program details 532 can include names of the programs, electrode assignments for the programs, the frequency of the programs, and/or other parameters associated with individual programs. In a particular embodiment, program details 532 include the numeric identifier of individual electrodes and a polarity assignment of individual electrodes. The numeric identifier of the electrode may correspond to an electrode identifier on a lead or other signal delivery device. The GUI 514 may also provide a CUSTOMIZE button 534 that enables a patient to assign customized names to individual programs displayed or available for program selection through the patient's controller application. For example, a patient may actuate or use the CUSTOMIZE button 534 to assign "day time" to program P1, "night time" to program P2, and "exercise" to program P3. In embodiments where the mobile device 500 is used as a practitioner's controller rather than a patient's controller, and in embodiments where the GUI 514 is a practitioner's controller application GUI, the customize button 534 can be used by a practitioner to set or otherwise define parameters, such as frequency, amplitude, and electrode assignment, for individual programs assigned to a patient.

The GUI 514 can allow a patient to vary the amplitude or intensity of signals delivered by the signal generator 101. For example, the GUI 514 may provide an input component 536 (e.g., a slider) to enable the patient to vary the amplitude between a minimum level and a maximum level. The GUI 514 may alternatively display a value in millivolts or milliamps in lieu of displaying "min" and "max". The minimum and maximum values can be predetermined by the physician to limit the minimum and maximum range of allowed amplitude variation, as desired. After varying the amplitude selection with input component 536, the patient or other user can save or execute the new amplitude selection by manipulating the ENTER button 538

The GUI 514 provides a pain report feature for periodically receiving feedback from the patient. The feedback can be used to help a practitioner determine the efficacy of a particular program. The pain report feature can include a pain report indicator 540 and several pain report input components 542a-j (collectively, the input component 542). The patient's controller application can alert, notify, or remind the patient to submit a pain report for a particular program selection by highlighting, flashing, blinking, or otherwise illuminating the pain report indicator 540. In one embodiment, the patient's controller application can alert the patient to submit a pain report after a predetermined period of time, after the patient selects a program, or after the patient alters a parameter of program. In another embodiment, the patient's controller application can alert the patient to submit a pain report periodically (e.g., twice a day, a few times a week, etc.) independent of program selection, changes to program selections, or changes to parameters of programs. In yet other embodiments, the patient's controller application can be configured to alert and/or request a pain report from the patient in response to sensor-related predetermined events. For example, a predetermined sensor-related event may include an impedance measurement between the electrodes of program P1 changing from 300 kiloohms to 20 kiloohms. In other words, the patient's controller application may request a pain report from the patient in response to a sensor measurement exceeding an absolute or relative threshold value associated with a particular sensor.

To submit a patient report, the patient can select from one of the input components 542 and then select the ENTER button 544 to submit the pain report. In one embodiment, the input components 542 can be radio buttons that are labeled from "1" to "10" (e.g., 1 being the lowest amount of pain and 10 being the greatest amount of pain). As discussed previously, the patient's controller application, the signal generator 101, the practitioner's controller 117, and/or the server 204 may use pain reports submitted by the patient to rate the efficacy of a particular program in order to assist the patient's physician as well as physicians of other patients in providing effective modulation therapy.

Throughout the description of the mobile device 500 and the GUI 514, various input components examples of various input components, i.e., radio buttons and slider, have been discussed. However, various other input components can also be used. For example, to provide instructions to the patient or to receive input from the patient, the patient's controller application GUI 514 may include pushbuttons, sliders, radio buttons, checkboxes, text boxes, pop-up menus, list boxes, toggle buttons, tables, button groups, active X controls, and the like.

To enable the mobile device 500 to communicate with the implanted signal generator 101, the mobile device 500 may be physically and communicatively coupled to a medical device communication module 546. The medical device communication module 546 may be physically attached to a communication port 548 of the mobile device 500. According to various embodiments, the communication port 548 can be a mini USB port, a micro-USB port, an Apple®-specific communication port, an audio port, an NV port, or other communication port supported by the mobile device 500. The medical device communication module 546 may be configured to convert signals received from the mobile device 500 into one or more communication protocols that are compatible with wirelessly communicating with the signal generator 101.

The physician for the patient may obtain access to the patient's controller application on the mobile device 500 using one or more tools or components described in the computing system 200. For example, the practitioner's controller 117 may interface directly with the patient's controller application via the medical device interface 246. However, because the mobile device 500 may be a personal consumer electronic device of the patient, and to protect the privacy of the patient, the practitioner's controller 117 may submit alterations or modifications to the programs assigned to the patient by transmitting the modifications to the server 204 via the network 208. Upon receipt of modifications to a patient's controller application, the server 204 may use the synchronizer 264 to distribute or push updates to the patient's controller application via the network 208. Alternatively, when the stub program 238 of the patient's controller 106, 500 checks the server 204 for updates, the stub program 238 may proactively download changes or modifications that were uploaded via the practitioner's controller 117. Although not shown, the patient's controller application GUI 514 may include an option to synchronize settings for the patient's controller application with corresponding settings that are mirrored in the server 204 for the patient's controller application. In other embodiments, a physician may use the webpage 262 instead of the practitioner's controller 117 to distribute or upload modifications to the patient's controller application. Upon receipt of changes to the patient's controller application via the webpage 262, the server 204 may push or distribute the received changes by using the synchronizer 264.

There are several advantages to integrating the patient's controller application into a personal consumer electronic device of the patient. Some of the advantages discussed include lower overhead cost both to the physician and the patient for providing patient's controller services; the patient will be more likely to keep the patient's controller in close proximity to the signal generator 101; and in the case that the mobile device 500 is a smart phone, regular or constant cellular or other network access to the mobile device 500 enables more readily accessible remote access to the signal generator 101.

Figure 6:
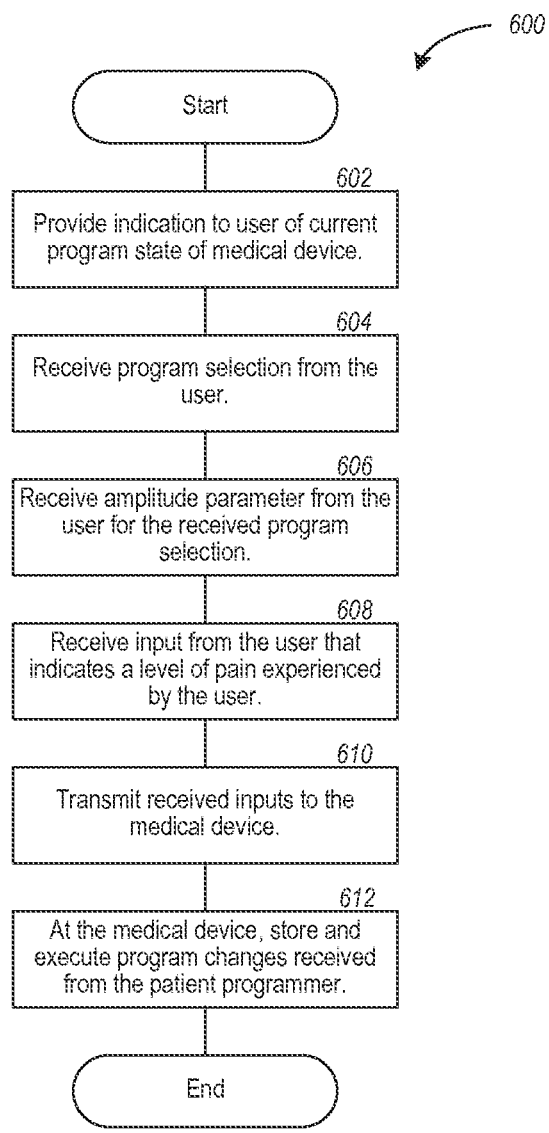
FIG. 6 is a flow diagram illustrating a method of operating the patient-operated controllers of FIGS. 4A-4C and 5 in accordance with embodiments of the present disclosure.

FIG. 6 illustrates a method 600 of operating a patient's controller, in accordance with an embodiment of the present disclosure. At block 602, the patient's controller provides an indication to a user of the current program state of a signal generator or other medical device. At block 604, the patient's controller receives a program selection from the user. At block 606, the patient's controller receives an amplitude parameter selection from the user that corresponds to the received program selection. For example, if a user selects a program P1, then the patient's controller can also receive an amplitude selection, such as LOW, MEDIUM, or HIGH, to further define how the medical device should execute the received program. At block 608, the patient's controller receives input from the user to indicate a level of pain experienced by user. As discussed above, this level of pain reported by the user can be correlated with a particular program to automatically change the program, to generate an alert to notify a healthcare professional, and/or to assist with determining the efficacy of a particular program. At block 610, the patient's controller transmits the received inputs to the medical device. The received inputs can include a program to be executed, an amplitude parameter associated with the program to be executed, and a level of pain reported by the user. At block 612, the medical device stores and executes the program changes and other inputs received from the patient's controller. By storing the inputs received from the patient's controller, the medical device allows a healthcare provider to extract the history of interactions between a patient and the medical device carried by the patient. In one particular embodiment of the present disclosure, the method 600 can be executed by a practitioner's controller, e.g., such as practitioner's controller 117, as will be described below in connection with FIGS. 7A-7Q.

Figure 7A:
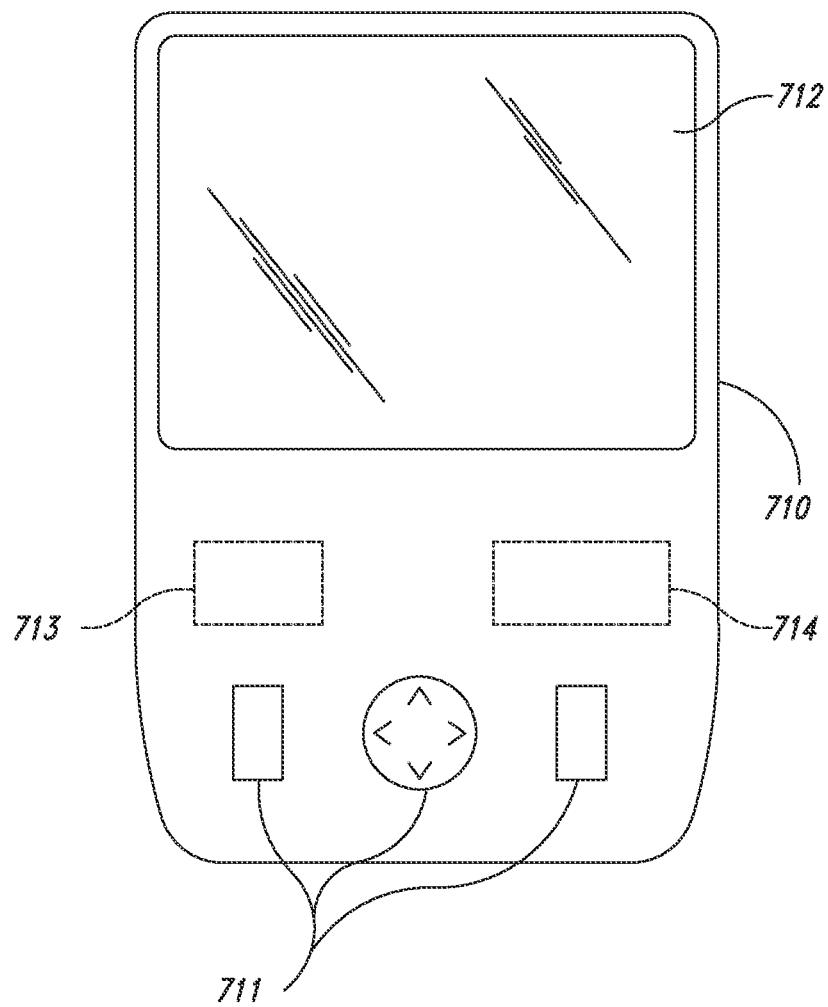
FIG. 7A is a schematic illustrating a practitioner-operated device in accordance with particular embodiments of the present disclosure.
Figure 7B:
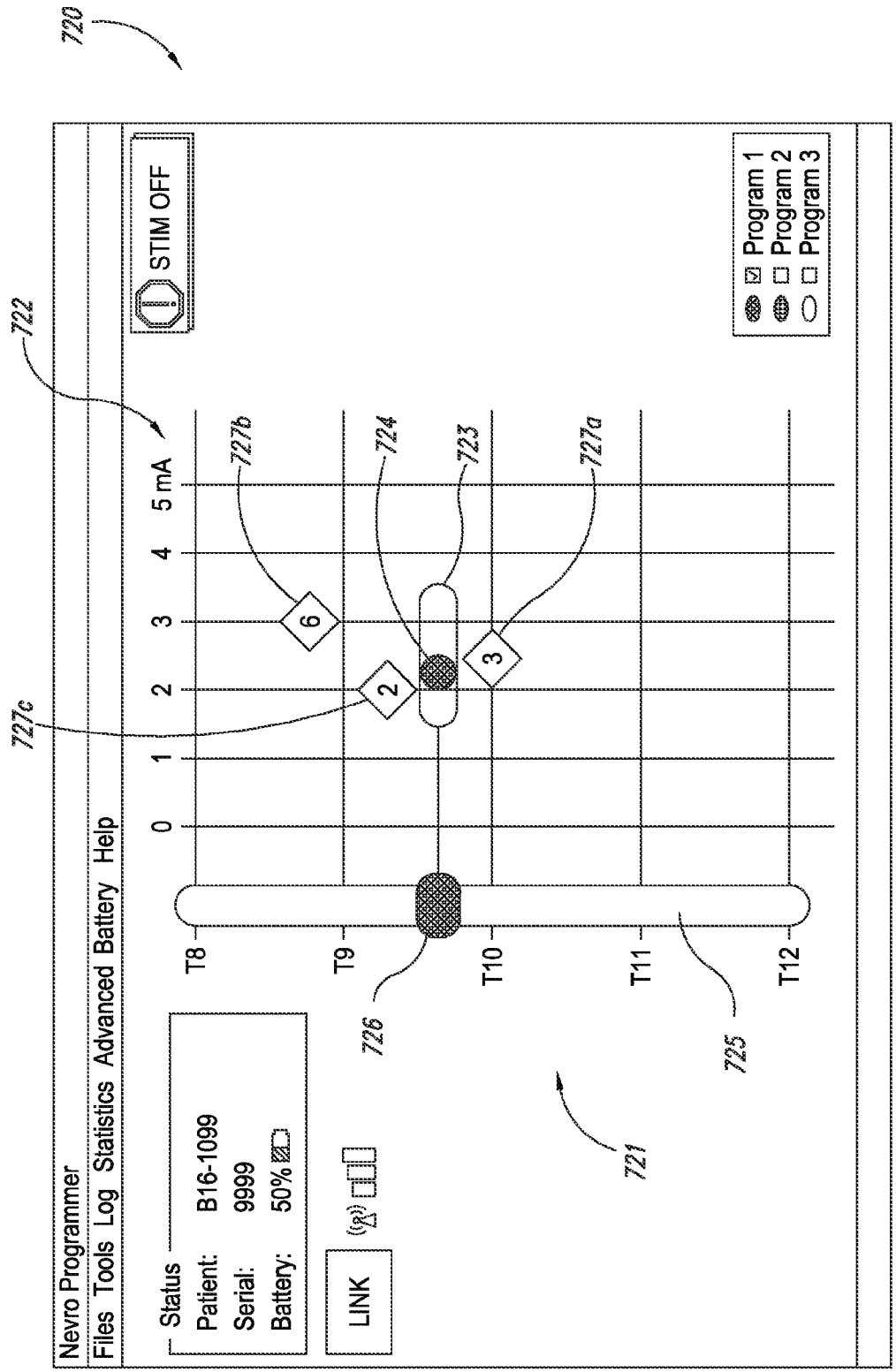
FIGS. 7B-7Q are schematics illustrating various implementations of a graphical user interface displayable by the practitioner-operated controller of FIG. 7A in accordance with particular embodiments of the present disclosure.
Figure 7C:
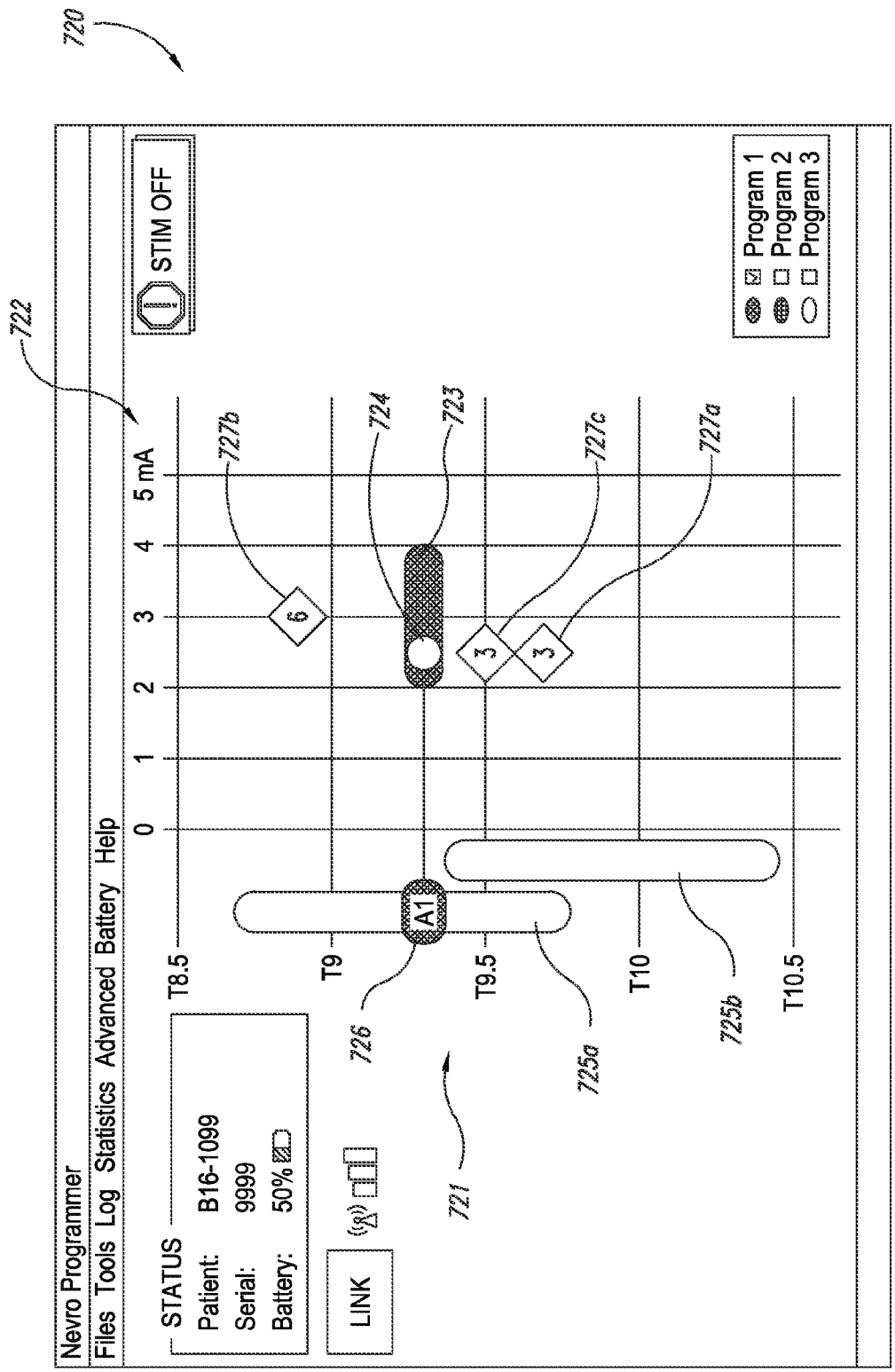
Figure 7D:
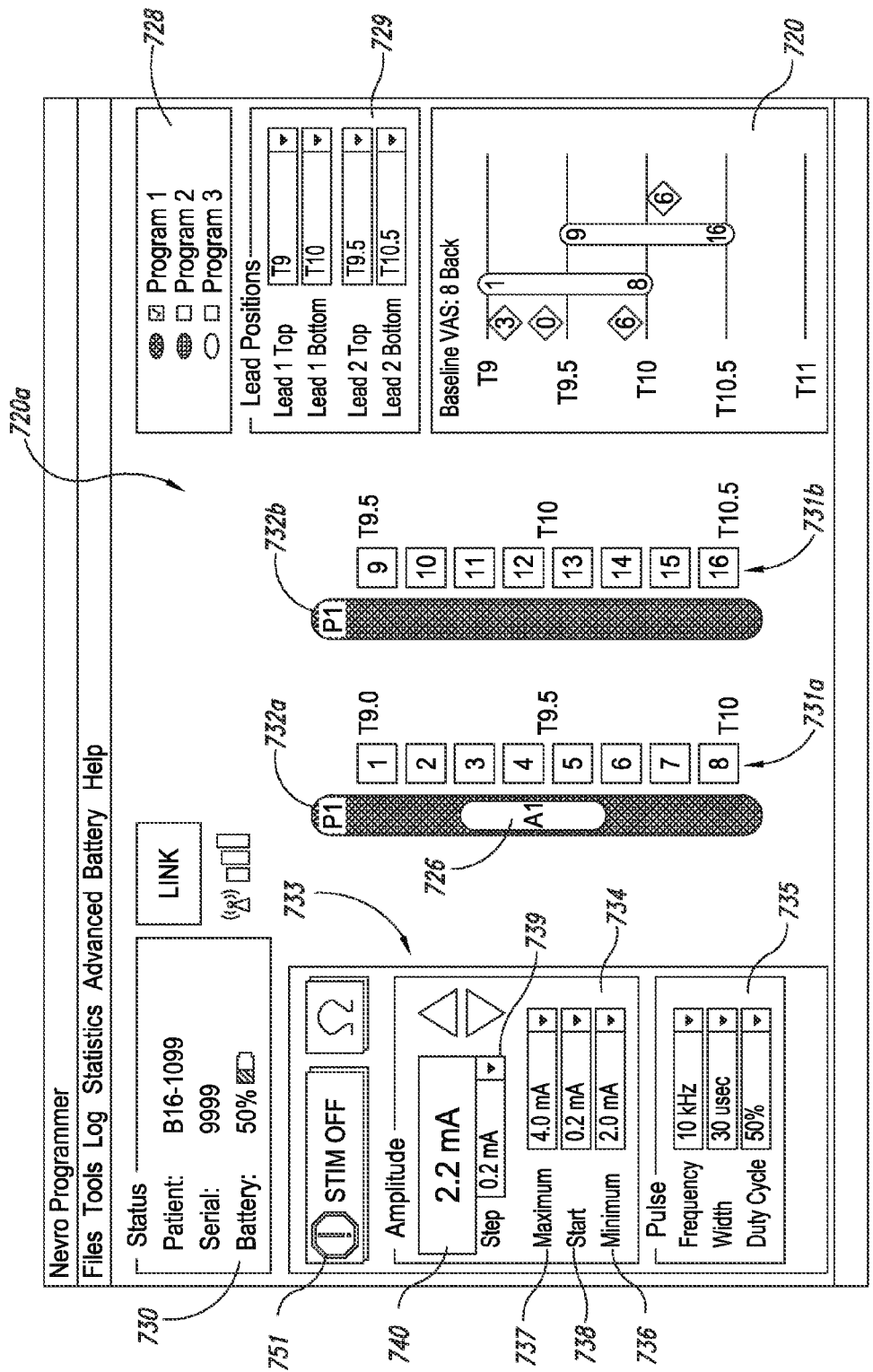
Figure 7E:
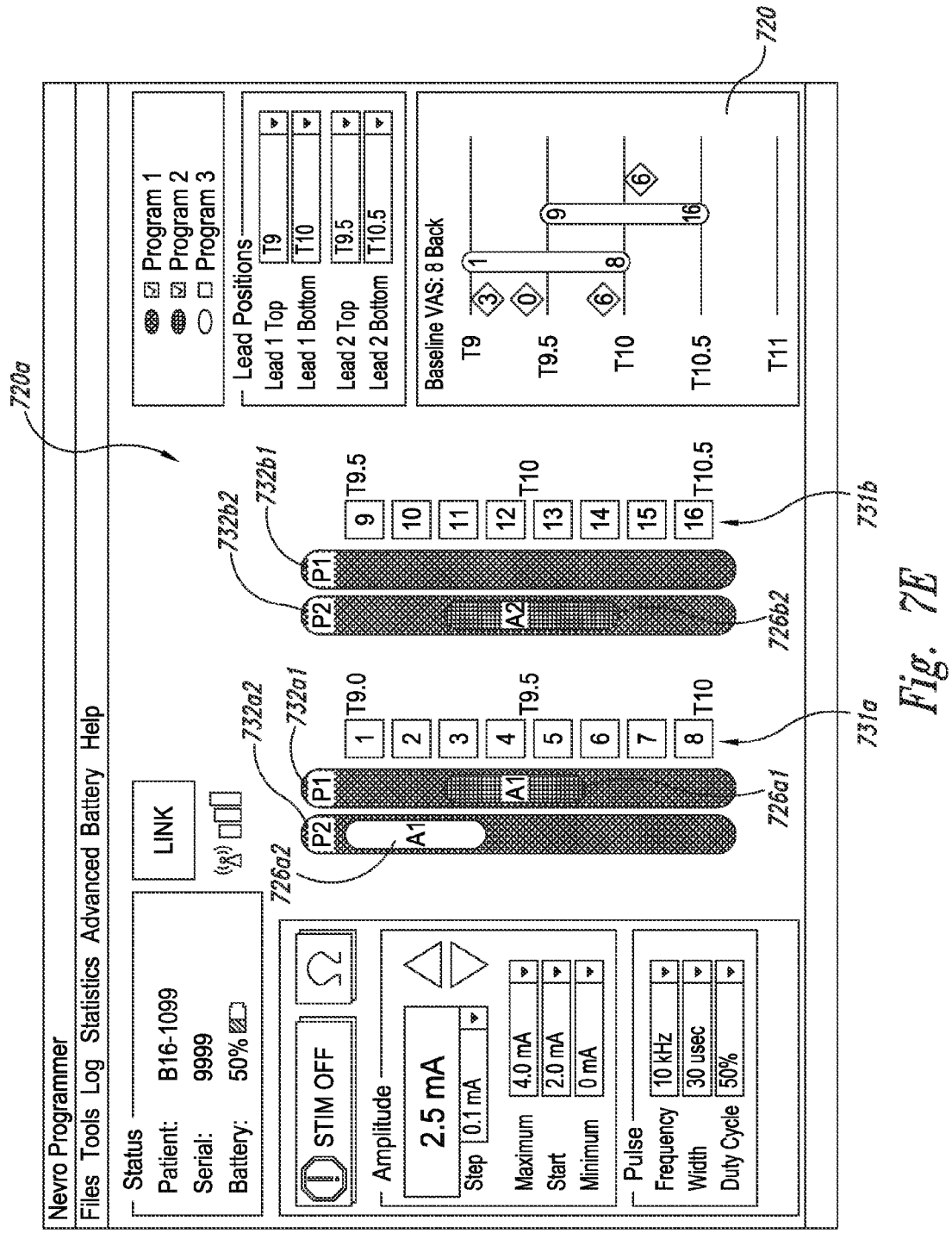
Figure 7F:
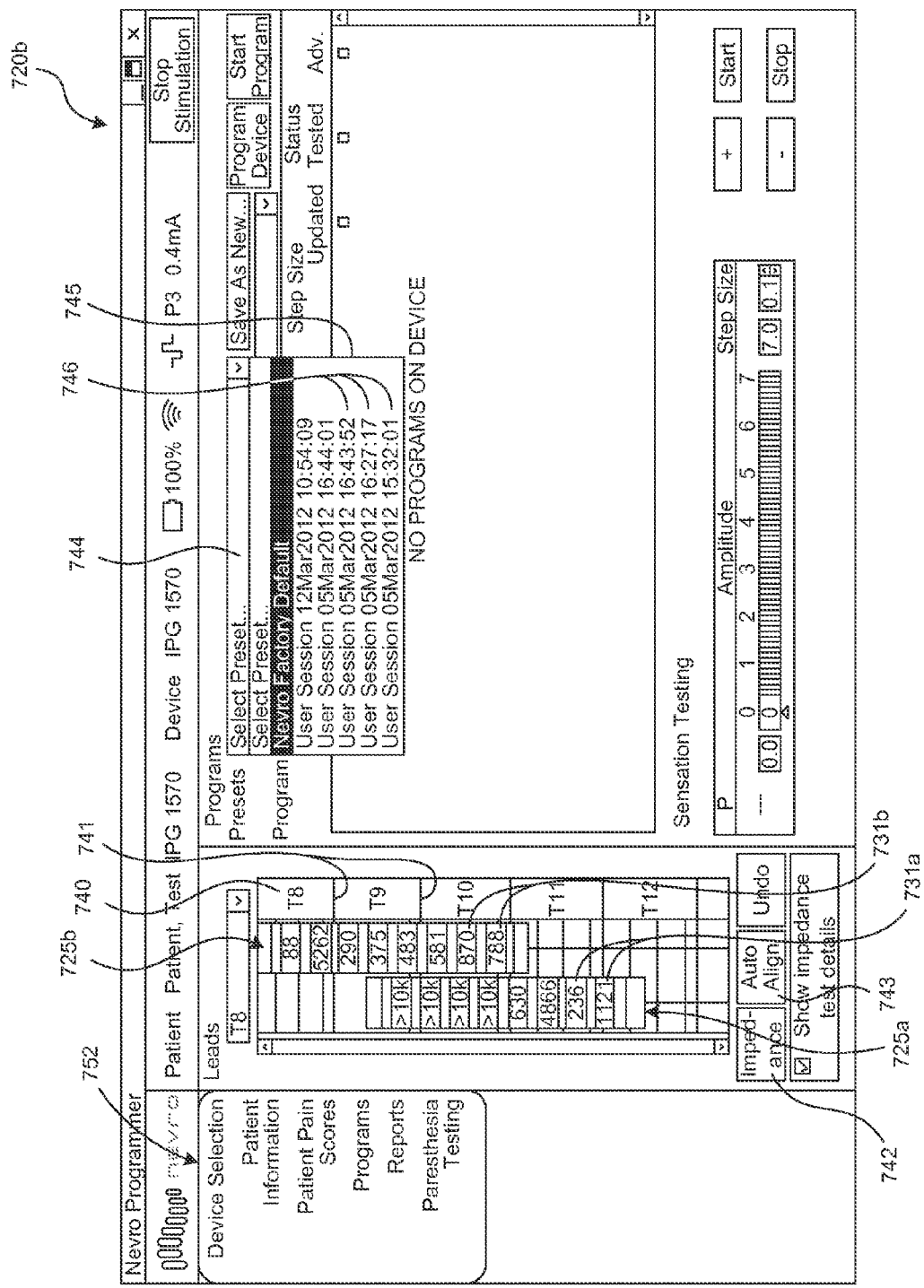
Figure 7G:
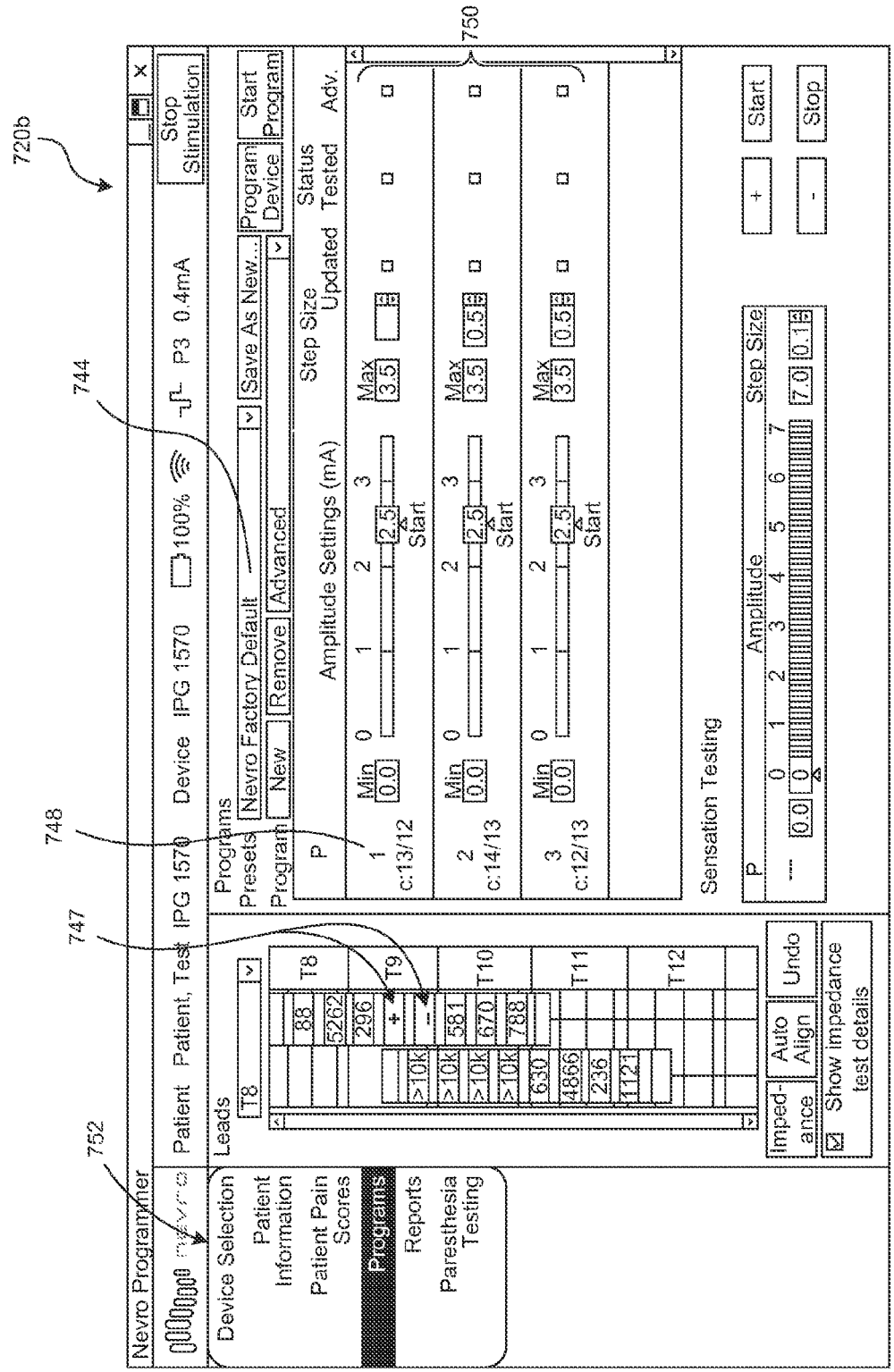
Figure 7H:
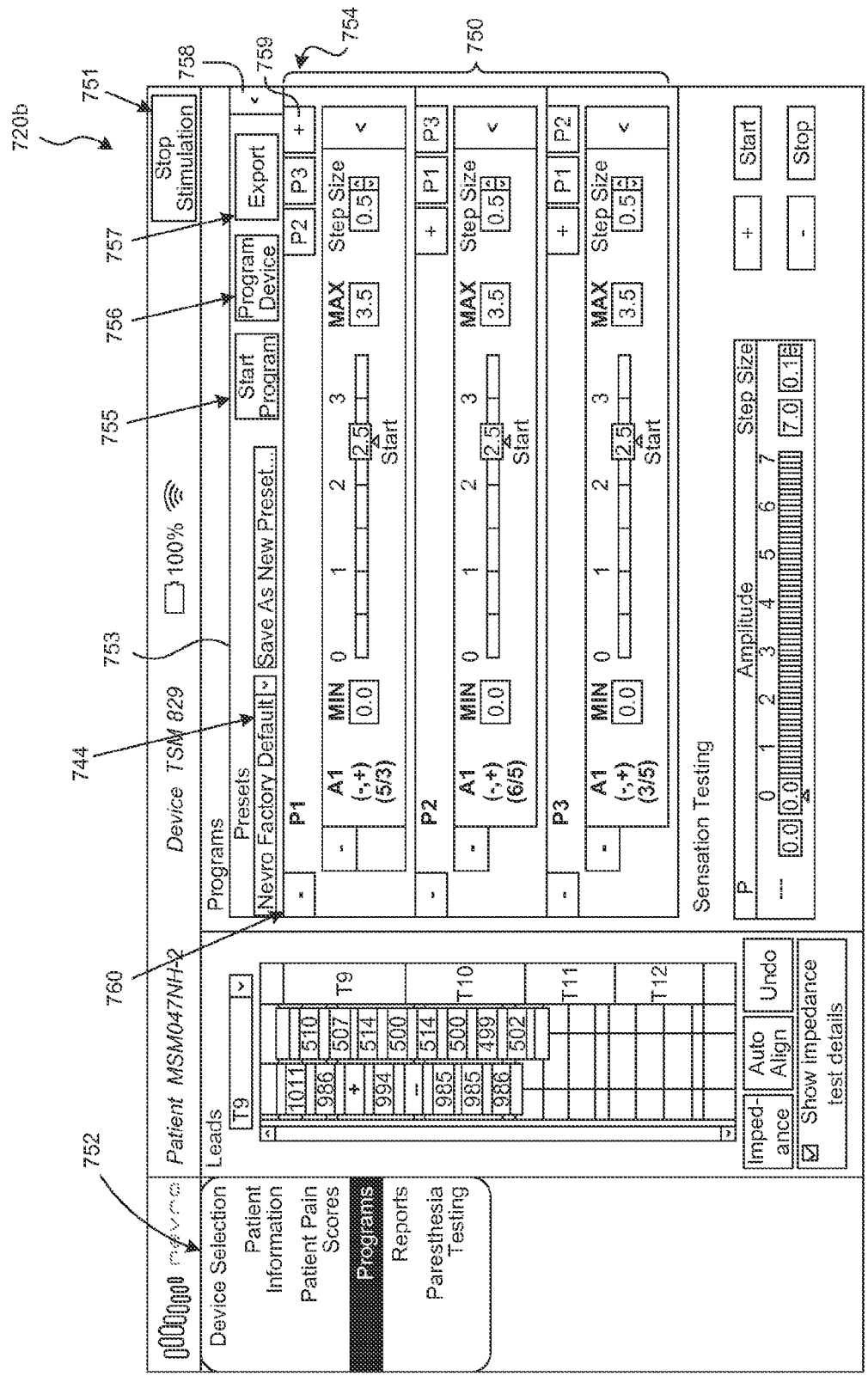
Figure 7I:
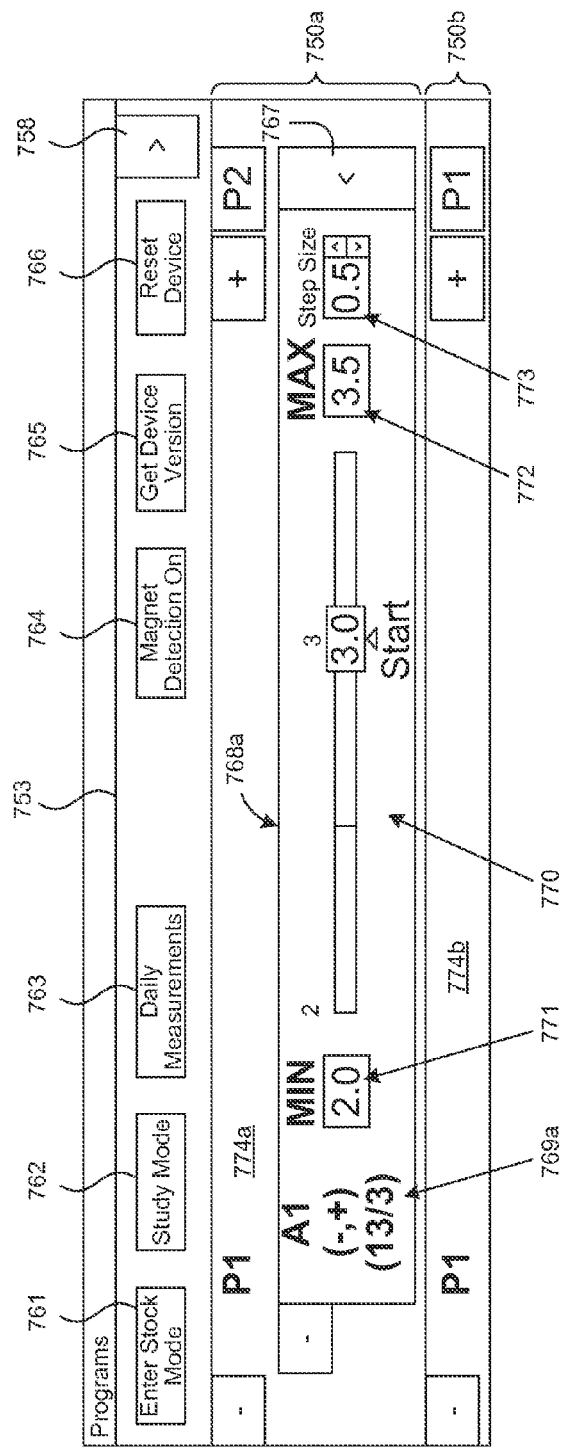
Figure 7J:
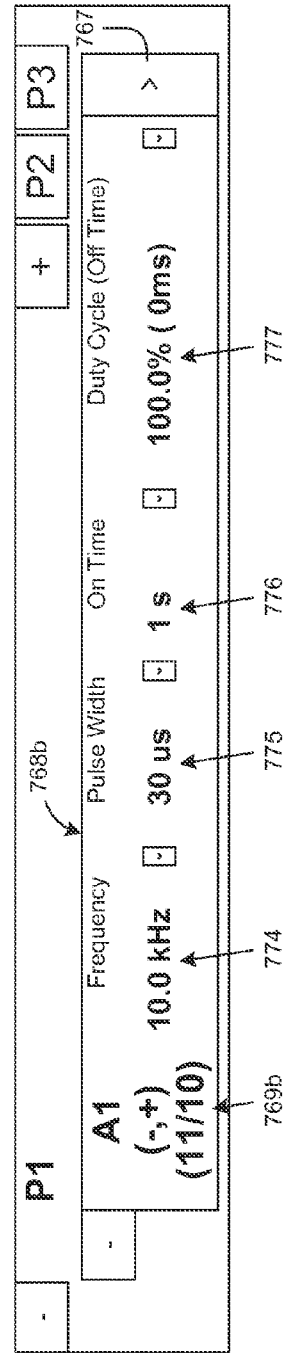
Figure 7K:
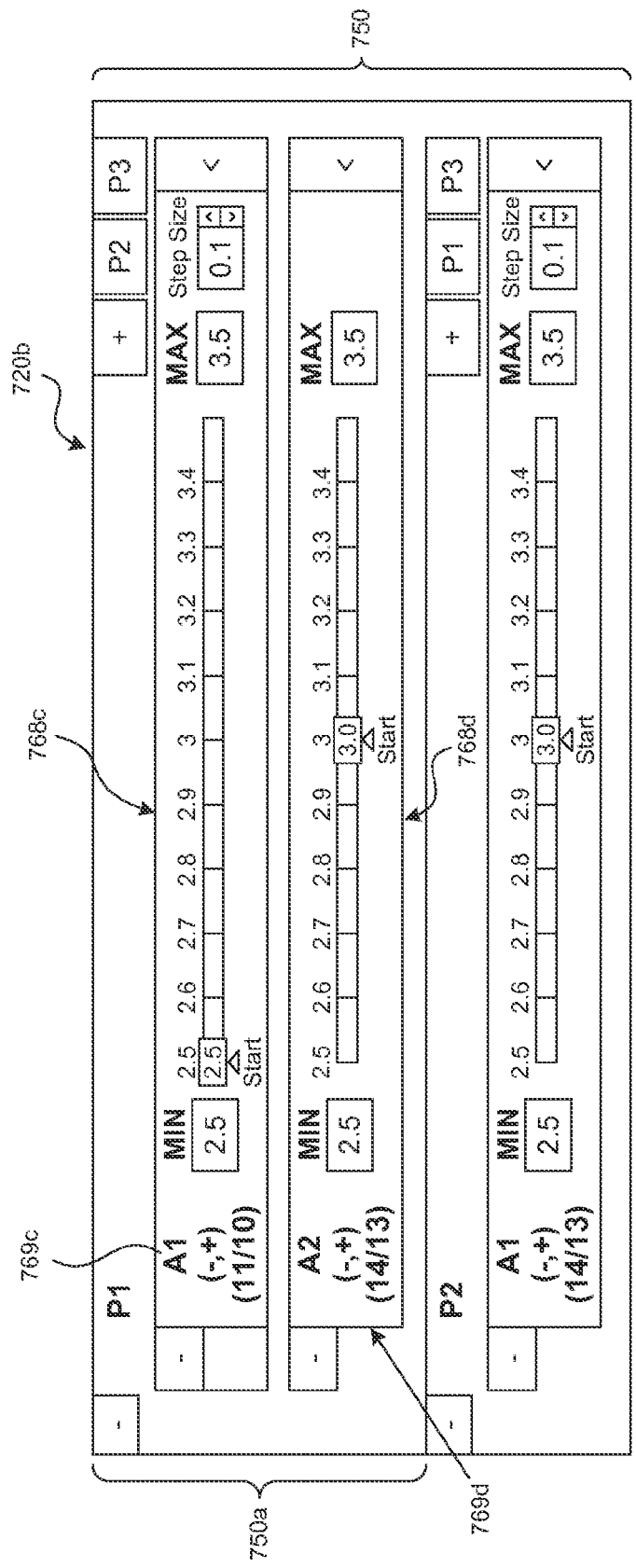
Figure 7L:
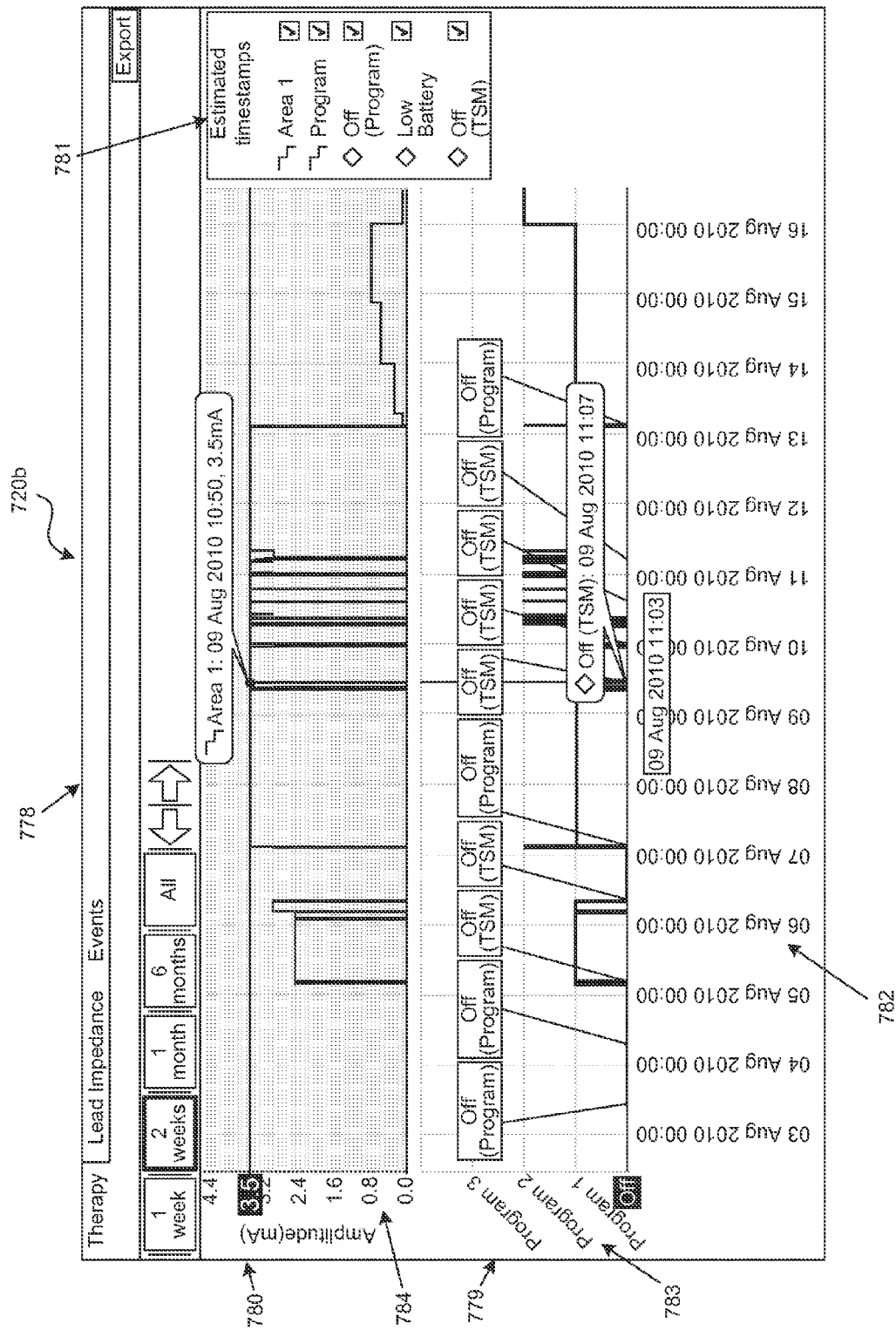
Figure 7M:
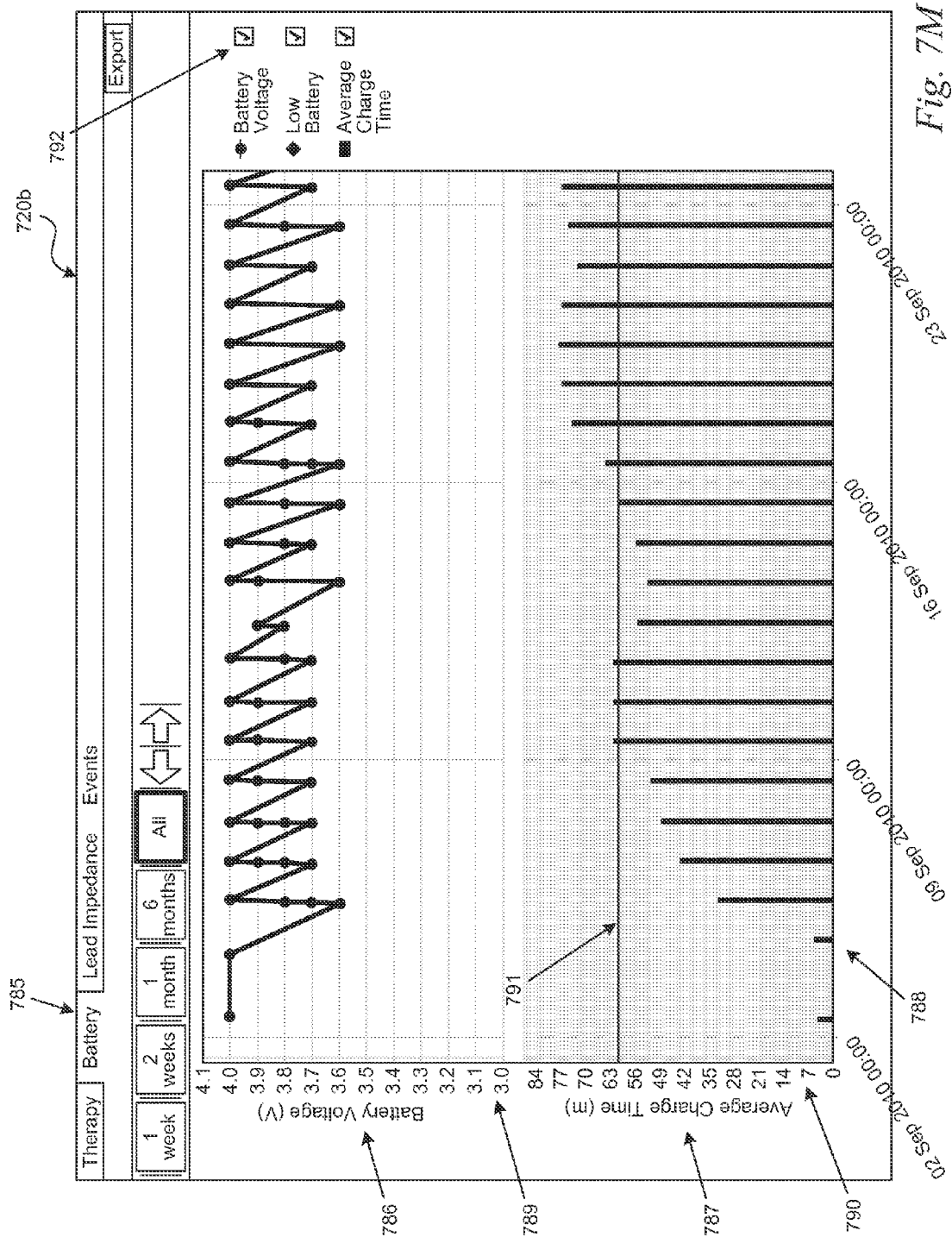
Figure 7N:
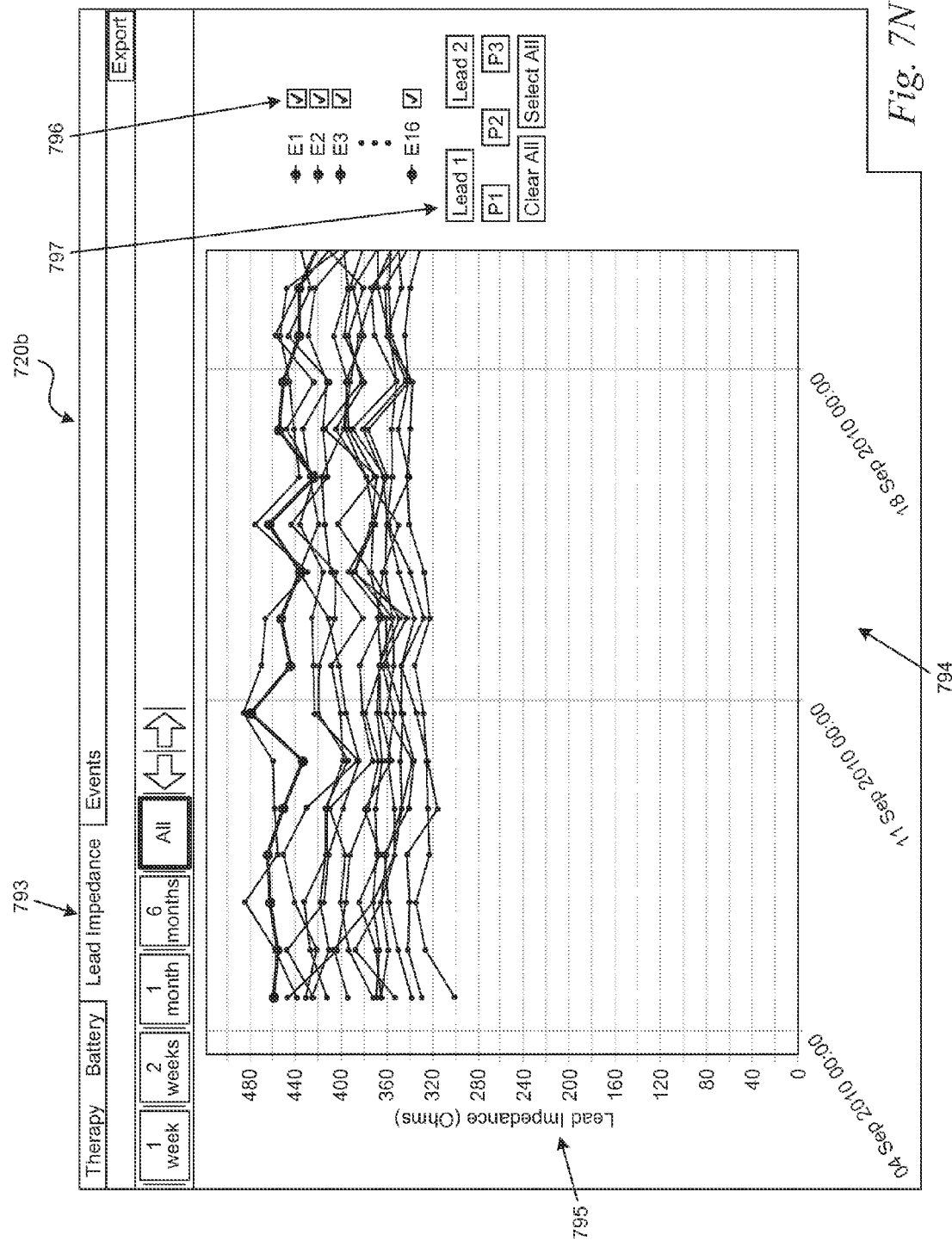
Figure 7P:
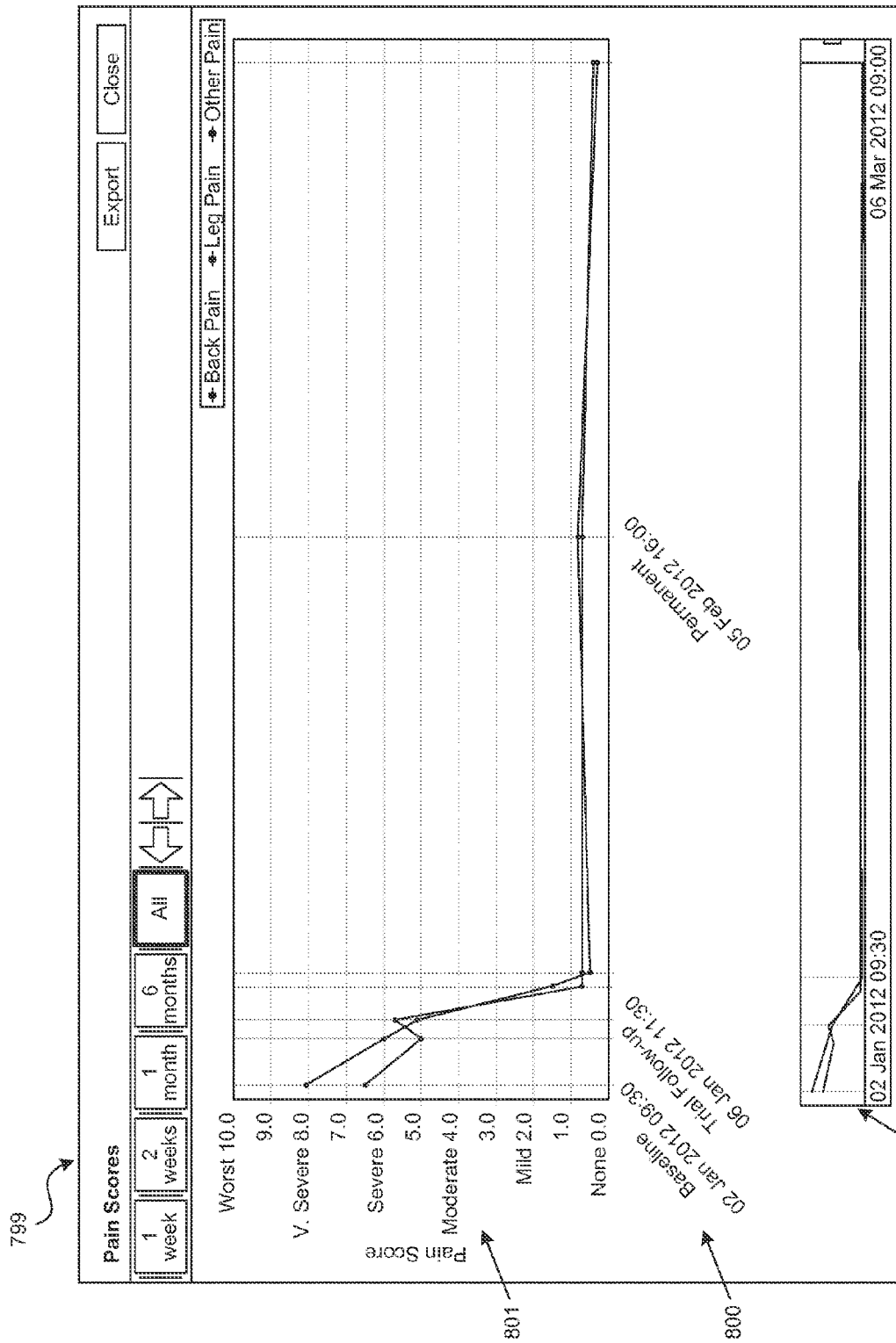
Figure 7Q:
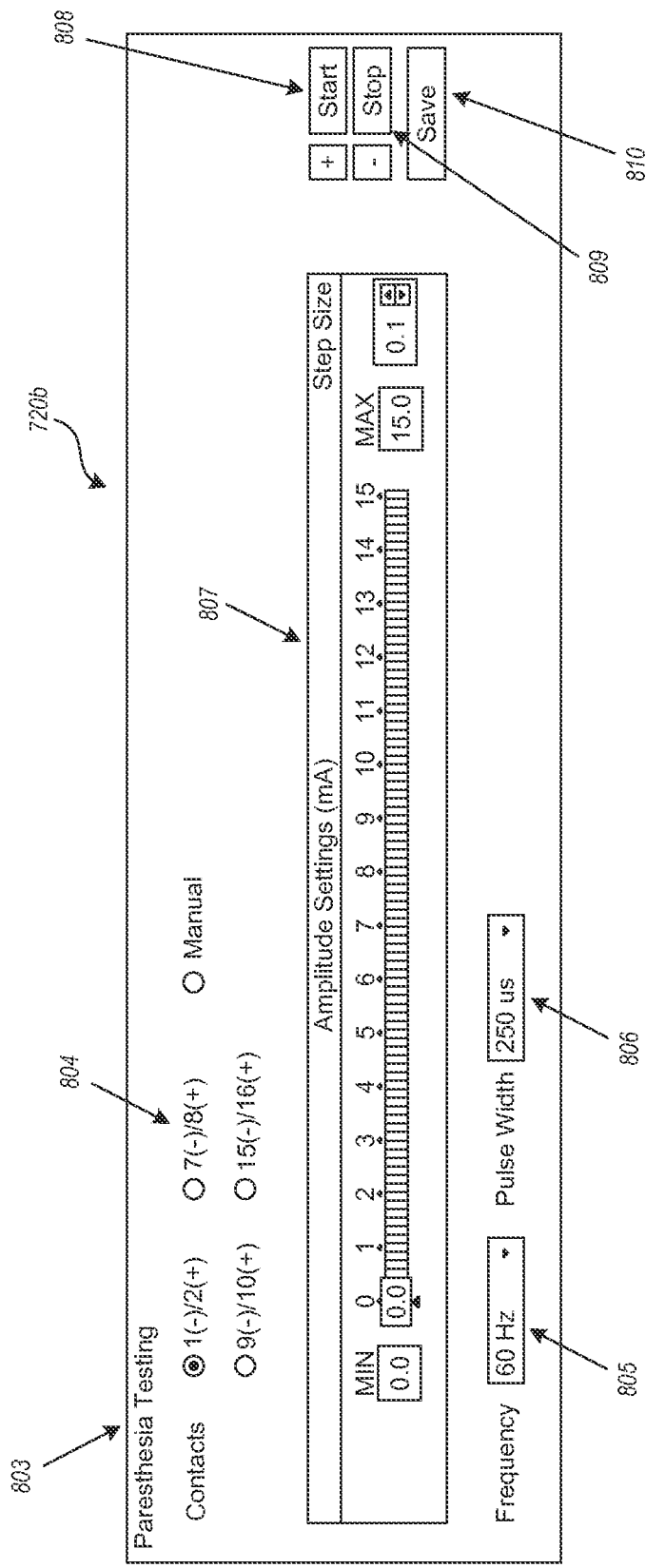

FIGS. 7A-7Q illustrate devices and associated methodologies that the practitioner can use to control the therapy provided to the patient. In general, these devices and methodologies allow the practitioner more control over the therapy than is typically granted to the patient. These features and methodologies can be implemented on a device that is temporarily hardwired directly to the lead (e.g., in the manner of the external programmer 105 described above with reference to FIG. 1A) or via a wireless link to an implanted signal generator (e.g., in the manner of the practitioner's controller 117, also described above with reference to FIG. 1A). The patient's controller 400, 500 and the practitioner's controller can each include different security keys, codes, or authorization arrangements that are automatically transmitted to and interpreted by the controlled device (e.g., the implanted signal generator). Accordingly, the controlled device can be controlled by either the patient's controller (e.g., in a first mode) or the practitioner's controller (e.g., in a second mode) as appropriate.

FIG. 7A schematically illustrates a practitioner's controller 710 having a display medium 712 (e.g., an LCD, LED array, or other suitable medium) and one or more input devices 711 that are used to input information displayed at the display medium 712. The practitioner's controller 710 can also include an internal memory 713 and processor 714 (and/or other computer/machine readable media) that store and execute programs and/or instructions associated with establishing and presenting signal delivery parameters at the display medium 712. If the controller 710 is connected directly to a lead or other signal delivery device, then it also includes an internal signal generator for generating the modulation signal. If the controller 710 is wirelessly connected to an implanted signal generator, then it can control the manner in which signals are generated by the implanted signal generator. According to various representative implementations of the present disclosure, the practitioner's controller 710 can be a desktop, laptop, netbook, or tablet computing device. The practitioner's controller 710 can also be implemented in a smart phone, personal digital assistant, or other computing device. Aspects of displays presented at the display medium 712 are described in further detail below with reference to FIGS. 7B-7Q.

FIG. 7B illustrates a representation of a display 720 that may be presented at the display medium 712 shown in FIG. 7A. The display 720 can include a two-dimensional, graphical layout, with a vertical axial scale 721 identifying axial locations along the patient's spine (e.g., from T8 to T12) and a lateral amplitude scale 722 identifying the current amplitude (e.g., in mA) with which a therapeutic signal is delivered to the patient. The display 720 also includes a therapy location identifier 726 indicating where along the axial scale 721 the modulation signal is applied, and an available amplitude window 723 that indicates the range of current amplitudes the practitioner has access to. An amplitude identifier 724 indicates the present amplitude level. Accordingly, the practitioner can move the therapy location identifier 726 up and down along the axial scale 721 (e.g., using a drag and drop routine or other suitable arrangement), and can adjust the amplitude of the signal by moving the amplitude identifier 724 back and forth (e.g., also using a drag and drop or other suitable arrangement).

The display 720 also includes one or more pain score identifiers 727 (three of which are shown in FIG. 7B as first, second, and third pain score identifiers 727a, 727b, 727c, respectively). The pain score identifiers 727 can identify numerical VAS scores (or other suitable index values) as a function of amplitude and axial location along the spine. The scores can be for the particular patient presently receiving therapeutic modulation, or for other relevant patients or patient populations. For example, the pain score identifiers 727 can reflect data for a patient population having symptoms or indications similar to those experienced by the present patient. Accordingly, the practitioner can view historical pain scores for a representative patient or patient population in the same manner and on the same display as are displayed the location and amplitude of the patient presently receiving therapeutic modulation. This can aid the practitioner in selecting an appropriate axial location and amplitude for the present patient. For example, the practitioner can locate the amplitude and axial location of the modulation at or proximate to the pain score identifier 727 with the lowest value (e.g., pain score identifier 727c). An advantage of this arrangement is that it presents historical information and adjustable patient parameters together in an easy-to-view and easy-to-manipulate format.

FIG. 7B illustrates a virtual representation of a single lead extending from about vertebral level T8 to about vertebral level T12. In other embodiments, the patient may have multiple leads implanted along the spine. For example, referring now to FIG. 7C, the display 720 presents a virtual representation of a first lead identifier 725a corresponding to a first lead implanted in a patient and a virtual representation of a second, inferiorly located, lead identifier 725b corresponding to a second lead implanted in a patient. Using the lead identifiers 725a, 725b as guides, the practitioner can manipulate the location and amplitude of the modulation provided to the patient, in the manner generally described above with reference to FIG. 7B. In the region where the two leads overlap, the practitioner can drag or otherwise move the therapy location identifier 726 laterally from one lead to another to select the lead that will apply the modulation signal. If the practitioner drags the therapy location identifier 726 above or below the axial extent of a particular lead, the program can automatically shift the therapy location identifier 726 to the adjacent lead, assuming the adjacent lead has the appropriate axial extent. In any of these embodiments, the program can automatically select the contacts on the lead that are closest to the therapy location identifier 726. Further aspects of this feature are described in greater detail below with reference to FIGS. 7D and 7E.

Referring now to FIG. 7D, the detailed display 720 described above with reference to FIGS. 7B and 7C has been simplified and made part of an overall display 720a. The overall display 720a can include a status identifier 730 (e.g., identifying the patient, device, and battery state), a program options indicator 728 (e.g., identifying available programs), a lead position summary 729, and a signal delivery parameter identifier 733. The overall display 720a can also include contact identifiers 731 for individual implanted leads. In the embodiment shown in FIG. 7D, the patient has two implanted leads and accordingly two corresponding sets of contact identifiers 731a, 731b. Next to contact identifier set 731a, 731b is a corresponding program identifier 732a, 732b which identifies an available program (e.g., program P1). The therapy location indicator 726 appears along the program identifier 732a to indicate the location at which the therapy is provided in association with that program. In the particular embodiment shown in FIG. 7D, the patient receives therapy centered approximately at vertebral location T9.5, via the left/superior lead and no therapy via the right/inferior lead.

As indicated above, the program can automatically select appropriate signal delivery contacts depending upon the location at which the practitioner places the therapy location identifier 726. For example, as shown in FIG. 7D, the practitioner has moved the therapy location identifier 726 to the illustrated location, and the program has automatically selected contacts "3" and "5" to deliver modulation over an area extending at least between these contacts. One feature of this arrangement is that the practitioner need not select which contacts are active. Instead, the practitioner can select the desired vertebral location (e.g., based on the pain score indicators 727) and allow the program to select the appropriate contacts. Another feature of this arrangement is that the practitioner need not select which of the active contacts is anodic or cathodic. As used herein, the cathodic contact refers to the contact that receives a negative or polarizing pulse at the outset of a pulse train in accordance with which the modulation is provided. As discussed above, it is believed that the presently disclosed therapy is insensitive or relatively insensitive to which contact in a bipolar pair of contacts is anodic or cathodic. Accordingly, the practitioner need not make this selection, which simplifies the practitioner's task of establishing program parameters for the patient. In particular, the practitioner controller 710 can be prohibited from accepting user inputs for cathode/anode selection. Instead, the program executed by the practitioner's controller 710 (or by the implanted signal generator with which it communicates) can automatically select which contact is anodic and which is cathodic without user input, in accordance with any of a variety suitable algorithms. For example, the program can select the superior contact to be cathodic, and the inferior contact to be anodic. In other embodiments, this relationship can be reversed.

In any of the foregoing embodiments described above with reference to FIG. 7D, the therapy location identifier 726 can be highlighted or otherwise differentiated when the practitioner has active control over the signal delivery parameters associated with the therapy provided at that location. For example, as shown in FIG. 7D, the therapy location identifier 726 is brightly displayed, indicating to the practitioner that the associated signal delivery parameters may be controlled by manipulating the signal delivery parameter identifiers 733. These identifiers can include pulse identifiers 735, and amplitude identifiers 734. The amplitude identifiers 734 can include a minimum amplitude 736, a maximum amplitude 737, a starting amplitude 738, an amplitude step identifier 739, and a present amplitude identifier 740. The practitioner can select the amplitude step and then adjust the amplitude between the minimum value and the maximum value, with the present value indicated by the present amplitude identifier 740. While testing various parameters, the practitioner can use the STIM OFF push button 751 to cause the practitioner's controller 710 or to cause the signal generator to discontinue delivery of modulation signals to the patient.

One feature of the arrangement shown in FIG. 7D is that the minimum amplitude 736 can be a non-zero value set by the practitioner or by the manufacturer. The present therapy however, often does not provide an immediately detectable sensation (e.g., paresthesia) that indicates to the patient that the therapy is operating. Accordingly, establishing a minimum amplitude level can prevent the patient or the practitioner from inadvertently selecting an amplitude that is too low to provide therapy, which may not be detected by the patient for some time. In a particular embodiment shown in FIG. 7D, the minimum amplitude is set at 2 mA. As discussed above, the minimum amplitude may have lower values (e.g., 1 mA or 0.5 mA) depending upon factors including patient-specific factors and/or indication-specific factors.

FIG. 7E is a partially schematic illustration of the display 720a, showing information relating to multiple leads, multiple programs, and multiple therapy location indicators. In particular, FIG. 7E illustrates the first contact identifier set 731a associated with a first lead, and the second contact identifier set 731b associated with a second lead. Two available programs ("P1" and "P2") are indicated for individual lead by program identifiers 732a1, 732a2 for the first lead, and program identifiers 732b1, 732b2 for the second lead. In this particular arrangement, the practitioner has selected modulation locations for both programs 1 and 2 at the first lead (as shown by first and second therapy location indicators 726a1, 726a2), and for only program 2 (as shown by a third therapy location indicator 726b2) at the second lead. The signal delivery parameters presented by the signal delivery parameter identifiers 733 are associated with the therapy provided at the first lead under program P2, as identified by the second location indicator 726a2, which is highlighted in FIG. 7E. The other selected therapy location indicators 726a1 and 726b2 are shown in gray scale. Accordingly, the practitioner can readily identify which program and therapy location the signal delivery parameter identifiers 733 correspond to.

Another feature shown in FIG. 7E is that the practitioner can, if desired, override the default contact selection procedure carried out by the program. For example, the program automatically selected the therapy areas to extend over three contacts for programs P1 and P2 at the first lead. In a particular embodiment, this can be the default selection process. For program P2 at the second lead, the practitioner has changed the length of the therapy location identifier 726b2 so that it extends over four contacts (contacts 11-14). In other embodiments, the practitioner can select the therapy area to extend over other lengths, shorter or longer than those shown in FIG. 7E. In general, the program can select the two contacts positioned at the superior and inferior extremes of the therapy area to be the active contacts.

One aspect of several of the embodiments described above is that the program and associated system can automatically select the active contacts based on an input (e.g., from the practitioner) corresponding to the vertebral level at which the therapy is to be applied. In further embodiments, the program can automate still further functions, in addition to or in lieu of the foregoing functions. For example, the program can automatically select contact locations and/or other signal delivery parameters based on an input corresponding to a patient indication, e.g., a single input corresponding only to a patient indication. Other inputs can include the features of the signal delivery device that is or is to be implanted, e.g., the type (lead or paddle), model number, manufacturer and/or other features.

FIG. 7F is a partially schematic illustration of a display 720b configured in accordance with another embodiment of the present disclosure. In this particular embodiment, the display 720b presents first and second lead identifiers 725a, 725b, each of which includes corresponding first contact identifiers 731a and second contact identifiers 731b. Individual contact identifiers can in turn include an impedance level associated with that contact. The practitioner can activate an impedance check button 742 to initiate an impedance check, which updates the values indicated by the contact identifiers 731a, 731b. On the basis of the impedance values associated with each contact, the program can automatically select particular contacts having an impedance value within an appropriate, pre-established range, which are located near a target vertebral level, and/or can reject one or more contacts having an impedance value that is outside the pre-established range. The program can also color code contacts based on whether the impedance value for a contact is within a pre-established range, e.g., red for an unacceptably low impedance, yellow for a marginally low impedance, green for an acceptable impedance, yellow for a marginally high impedance, and red for an unacceptably high impedance. Table 1 shows, examples of color-coded impedance ranges in accordance with an embodiment of the present disclosure.

TABLE 1

| OHMS | COLOR | SUMMARY DISPLAY |
|---|---|---|
| <=50 ohms | RED | L or LOW |
| 51-199 ohms | YELLOW | L or LOW |
| 200-2999 ohms | GREEN | Contact # |
| 3000-7999 ohms | YELLOW | H or HIGH |
| >=8000 ohms | RED | H or HIGH |

The practitioner can adjust the relative location between the leads and the illustrated vertebral levels to match or closely correspond to the actual relative locations of the leads in the patient's body, using any of a number of suitable methods. For example, the practitioner can "drag and drop" one of the lead identifiers 725a, 725b so that it is properly aligned with the adjacent vertebral level identifiers 740. If the patient's vertebral levels do not have the axial dimensions illustrated at the display 720b, the practitioner can alter these dimensions. For example, the practitioner can drag and drop individual boundaries 741 between adjacent vertebral level identifiers 740 to adjust the axial extent of individual vertebral level identifiers 740. In addition to or in lieu of the foregoing, the practitioner can scale all the vertebral levels simultaneously with a single control. The practitioner can move the lead identifier 725a, 725b and/or manipulate the boundaries 741 between vertebrae based on viewing an image of the implanted lead(s) via an x-ray or other imaging protocol.

Once the practitioner has properly located one of the lead identifiers 725a, 725b relative to the adjacent vertebral level identifiers 740, the practitioner can request that the program automatically adjust the location of the other lead identifier relative to the first by activating an "auto align button" 743. The program can automatically align one lead identifier relative to the other based upon measured data, for example, the impedance data associated with contacts on one or both leads.

The display 720b can also include a preset window 744. When the practitioner clicks on the preset window 744, a preset menu 745 appears and lists multiple preset identifiers 746. In a particular embodiment, individual preset identifiers 746 can be labeled with a patient indication that may be addressed by one or more of the contacts located at the vertebral levels indicated by the vertebral level identifiers 740. For example, with the contacts positioned between T8 and T12, the preset identifiers 746 may correspond to "low back pain," "leg pain," and/or other patient indications that may be treated by activating contacts at these vertebral levels. In other embodiments, for example, when the leads are located at cervical vertebral levels, a different list of preset identifiers 746 appears when the practitioner activates the preset window 744.

The display 720b can also include a menu 752. The menu 752 can provide various optional views of the display 720b for the practitioner to select from. In the embodiment of FIG. 7F, the menu 752 includes options for device selection, patient information, patient pain scores, programs, reports, and paresthesia testing. The practitioner can select one of the menu options, such as programs, and the practitioner's controller can render the corresponding user interface elements on display 720b.

FIG. 7G illustrates the display 720b after the practitioner has selected one of the preset identifiers 746 shown in FIG. 7F. In this particular embodiment, the practitioner has selected the "Nevro Factory Default" preset identifier, which can correspond to an indication of low back pain, and can have associated descriptive text (not shown) and/or other indicia, such as an icon or audible tone, to further identify the preset as suitable for treating low back pain. In response, the program presents available modulation program identifiers 750, each of which corresponds to an available individual modulation program. Individual modulation programs can include a vertebral level (or location within a vertebral level) along with associated signal delivery characteristics, for example, frequency, pulse width and amplitude. The overall program and/or an individual modulation program can automatically identify and select the contacts closest to that vertebral level. The practitioner has the option of modifying at least some of these pre-set parameters, e.g., the maximum and minimum amplitudes associated with the particular modulation program. The practitioner can select one of the available modulation program identifiers 750 resulting in a selected modulation program identifier 748 which is highlighted or presented in a different color, or otherwise indicated to be distinct from the remaining available modulation program identifiers 750. The display 720b can also identify the active contacts associated with the selected modulation program via active contact identifiers 747. In several embodiments, the active contact identifier 747 presents the active contacts in a different color and/or presents a "plus" or "minus" sign within the active contact identifier 747. As discussed above, while the contacts may be indicated as positive or negative, the practitioner need not (and may not) have control over whether an individual contact is considered anodic or cathodic.

The active contacts can automatically be selected by the overall program that is associated with the preset identifier 746 (FIG. 7F) selected by the practitioner and displayed in the preset window 744. For example, if the user selects a particular modulation program intended for treating low back pain, that modulation program can have a predetermined correlation between active contacts and a vertebral level. The modulation program can have a predetermined requirement that the fourth contact down from the top of the lead be at approximately the middle of vertebral level T9, and the other contact of an active contact pair should be the next adjacent contact closest to the middle of vertebral level T9. If one or more of the contacts are unavailable (e.g., due to out-of-range impedance or an impedance that differs from a target value) the overall program and/or an individual modulation program can automatically select the pair of contacts closest to the target level.

FIG. 7H illustrates an embodiment of the display 720b that includes additional features available to a practitioner for defining, modifying, or otherwise making use of modulation program identifiers 750. For example, the display 720b includes a programs menu 753 and a programs list 754. The programs menu 753 includes the presets window 744, a start program button 755, a program device button 756, and an export button 757. The start program button 755 enables the practitioner to cause the signal generator to execute the programs identified by the modulation program identifiers 750. The program device button 756 enables the practitioner to transfer the modulation programs to the signal generator and to the patient controller to allow the patient to selectively operate programs on the signal generator. The export button 757 transfers the modulation programs with corresponding defined parameters to an Excel sheet, a data file, a database located on the patient's controller, and/or a server configured to receive, compile, order, and/or analyze the programs with corresponding rankings or ratings. The programs menu 753 also includes a menu button 758 for switching between a first set of program manipulation options and a second set of program manipulation options. Additional features available from the programs menu 753 are illustrated in FIG. 7I and will be discussed further below.

The programs list 754 displays modulation programs included in the modulation program identifiers 750. The programs list 754 can display all the modulation programs included in the modulation program identifiers 750, in some embodiments of the present disclosure. The programs list 754 lets a practitioner view the programs the practitioner has open and available for transfer to the signal generator. The programs list 754 can include all of the programs that have recently been defined or imported by the physician from the time the physician initiated a session or an instance of the practitioner controller program. In some embodiments, the programs list 754 includes all programs that a physician has assigned to a particular patient, such as the patient having the identification of MSM047NH-2. In other embodiments, the programs list 754 includes all programs that a physician has assigned to a particular device, such as the device having the identification TSM 829. The programs list 754 advantageously includes buttons labeled with names of modulation programs that the practitioner can select for viewing or that the practitioner can switch between. The programs list 754 can also include an add program button 759 and a remove program button 760. The add program button 759 can be used for adding and defining additional modulation program identifiers. The remove program button 760 can be used for removing programs from the practitioner's controller, the patient's controller, or the signal generator. In one particular embodiment, the practitioner's controller populates the programs list 754 when the practitioner's controller reads or receives modulation programs stored on the signal generator. The practitioner's controller can then remove modulation programs from the signal generator using the remove program button 760 to remove a program. Subsequently, in response to a selection of the program device button 756, the practitioner's controller can reprogram the signal generator with the modulation programs that have not been removed from the modulation program identifiers 750.

FIGS. 7I-7K illustrate additional features of the programs menu 753 from FIG. 7H. The practitioner's controller can display these additional features in response to the practitioner selecting the menu button 758. In the illustrated embodiments, the programs menu 753 includes two sets of features, as illustrated in FIGS. 7H and 7I. However, in other implementations, the programs menu 753 can include more or fewer than two sets of features. In the second set of features illustrated in FIG. 7I, the programs menu 753 includes an enter stock mode button 761, a study mode button 762, the daily measurements button 763, a magnet detection on button 764, a get device version button 765, and a reset device button 766. The enter stock mode button 761 can cause the practitioner's controller to enter a default mode that includes, for example, two or three programs that have been pre-selected for the stock mode. Selection of the study mode button 762 can cause the practitioners programmer to collect real-time information from the signal generator, such as electrical characteristics of the leads, voltage current levels of the battery, the amplitude, the program, the amplitude parameter being executed by the signal generator, measurements obtained by the accelerometer and other sensors carried by the signal generator, or the like. Selection of the daily measurements button 763 can cause the practitioners programmer to, for example, acquire up to 24 hours of operational history data from the signal generator and display the data in one or more reports which will be discussed in more detail below. Selection of the magnetic detection on button 764 can cause the practitioner's controller to discover signal generators located within a predetermined range of the practitioner's controller. Selection of the get device version button 765 can cause the practitioner's controller to request and receive hardware, firmware, and/or software information from the signal generator for display in the display 720b. Selection of the reset device button 766 can cause the practitioner's controller to transmit signals to the signal generator to cause the signal generator to reset itself.

Individual modulation program identifiers 750, e.g., modulation program identifier 750a, include a menu button 767 for switching between one or more program parameter screens 768 (identified individually as program parameter screens 768a-768d), as shown in FIGS. 7I-7K. Individual program parameter screens 768 can include multiple adjustable parameters that are available to the practitioner for customizing individual modulation programs. The user interface elements of the program parameter screens 768 can also enable the practitioner to define limits or place limits on parameter adjustments that are available to the patient on the patient's controller.

In a particular embodiment, the program parameter screen 768a includes an amplitude identifier 769a, and amplitude adjustment element 770, a minimum value input element 771, and a maximum value input element 772. The amplitude identifier 769a can include an alphanumeric reference, such as amplitude 1 or "A1", a numeric indication of the lead contacts assigned to the modulation program, e.g., (13/3), and signal polarity assignment of individual contacts. For example, in the illustrated embodiment, contact number 3 is assigned as a positive polarity electrode, and contact number 13 is assigned as a negative polarity electrode. However, as discussed above, the signals delivered by the contacts 3 and 13 may be polarity independent and can be unaffected by the positive and negative polarity assignments given to specific contacts on the signal delivery leads. The amplitude adjustment element 770 is illustrated as a user interface slide element that can be dragged from left to right to adjust the amplitude of the modulation program signal. In other embodiments, the amplitude adjustment element can be a text box, a multidirectional button, or other user interface input element that enables the practitioner to vary the amplitude within the range of the minimum and maximum amplitude values. The minimum and maximum amplitude values can be set by the practitioner using the minimum value input element 771 and the maximum value input element 772. According one embodiment, once the minimum and maximum amplitude of the modulation program signal has been set using the minimum value input element 771 and the maximum value input element 772, the patient controller cannot adjust the amplitude of the modulation program signal to a value that is outside of the defined minimum and maximum values.

The limitation of minimum and maximum amplitudes can be useful in accounting for the gradual wash-in and/or wash-out nature of pain and signal effectiveness while prescribing therapy. Gradual wash-in and/or wash-out of pain and signal effectiveness can be a characteristic of the frequency ranges, amplitudes, pulse widths, and/or other therapy signal parameters used by the modulation programs disclosed herein. For example, a patient might not feel the effects of the new adjustment or program until one to two hours after the adjustment, so a physician may want to limit the minimum or maximum amplitudes to account for the potential wash-in and/or wash-out nature of the disclosed therapy.

The step size input element 773 allows the practitioner to define the increments by which the amplitude adjustment element 770 and by which the patient controller can adjust the amplitude of the modulation program. It may be beneficial to define the step size so that the range of amplitudes between the minimum and maximum available amplitude values can be traversed in three or less steps, so as to provide the patient with less options and to provide the patient with increased peace of mind regarding whether or not the patient could make a further adjustment to further decrease any discomfort being experienced.

Individual modulation program identifiers 750 can be color-coded or color-coordinated with the contact identifiers 731 of the lead identifiers 725 of FIG. 7F. For example, a program list bar 774a of the modulation program identifier 750a can be highlighted with a particular color (e.g., blue) when the modulation program identifier 750a is selected for execution and/or modification. Then, to facilitate visual reference to the corresponding electrode contacts identifiers 731, the lead contact identifiers corresponding to the contacts shown in the amplitude identifier 769a are highlighted in the same color as the program list bar 774a. Similarly, a program list bar 774b of the modulation program identifier 750b can be highlighted in a different color than the color used to highlight the program list bar 774a. By color coordinating the modulation program identifiers 750 and the contact identifiers 731, the practitioner can easily see which contacts the practitioner has assigned to a particular modulation program identifier 750a, 750b.

FIG. 7J illustrates additional parameters available in program parameter screens 768, in accordance with an embodiment of the present disclosure. The program parameter screen 768b includes an amplitude identifier 769b, a frequency input element 774, a pulse width input element 775, a pulse duration input element 776, and a duty cycle input element 777. The frequency input element 774 allows the practitioner to define the frequency of the modulation program signal. The pulse width input element 775 defines the duration of each pulse within each period of the modulation program signal. According to one embodiment, the pulse duration input element 776 defines or sets a duration of time (i.e., an "on-time") for which a modulation program will deliver each individual series of pulse cycles when it is executed. The duty cycle input element 777 allows a practitioner to adjust the total amount of time that pulse cycles are delivered while the modulation program is active. In particular, the duty cycle input element 777 allows the practitioner to enter or select a percentage value that corresponds to a percentage of a total amount of time that any pulse cycles are delivered. The duty cycle input element 777 can also provide a corresponding indication of the amount of time between delivery of each individual series of pulse cycles (i.e., an "off-time" during which no pulse cycles are delivered). For example, a one second on-time with a 50% duty cycle would result in the sequential delivery of one second intervals of pulse cycles (i.e., one second of on-time) separated by one second intervals of off-time.

Although the program parameter screens 768a, 768b (collectively, the program parameter screens 768) described periodic square wave signals for modulation programs, additional program parameters screens can be added to allow the practitioner to define other types of modulation program signals. For example, the menu button 767 can be selected to display additional program parameter screens 768 to enable the practitioner to define the parameters of a triangle wave, a ramp wave, a sinusoidal wave, or other customized periodic signals. In other embodiments, the program parameter screens 768 can include parameters to enable the practitioner to define non-periodic signal patterns for repeated delivery to the signal delivery leads. For example, the program parameter screens 768 can include a graphical input element that allows the practitioner to draw the amplitude of the signal to be generated and delivered to the patient.

FIG. 7K illustrates another variation of the modulation program identifiers 750, in accordance with an embodiment of the present disclosure. As shown, individual modulation program identifiers 750 can have one, two, or more signals independently and concurrently generated from multiple sets of contacts. For example, the modulation program identifier 750a can include a modulation program P1 having two program parameter screens 768c and 768d. The individual program parameter screens 768c and 768d can each have their own corresponding amplitude identifiers 769c and 769d to indicate contact lead assignments, polarity of the contact leads, and the amplitude associated with individual signals. Although not shown in FIG. 7K, individual program parameter screens 768c and 768d can be associated with extended parameter screens whereby the practitioner can define further characteristics of the modulation program signals, such as frequency, pulse width, duty cycle, and on-time, as shown in FIG. 7J.

Enabling a practitioner to assign multiple signals concurrently and using different contacts can allow the practitioner to better customize the therapy provided to a patient. For example, by delivering the modulation program signal of amplitude identifier 769c, the practitioner can provide therapy for lower back pain while concurrently delivering modulation program signals of amplitude identifier 769d to provide therapy to a patient's leg pain. Thus, the portion of the display 720b that is illustrated in FIG. 7K can advantageously enable a practitioner to independently and/or concurrently define modulation program signals to provide therapy for different ailments experienced at different locations of the patient's body.

Referring briefly to FIG. 7F, the menu 752 includes various tabs or selections. The foregoing description of FIGS. 7F-7K has generally been associated with the "Programs" tab. Hereafter, the description of FIGS. 7L-7N are associated with the "Reports" tab of the menu 752. The description of FIGS. 7O-7P are associated with the "Patient Pain Scores" tab, and the description of FIG. 7Q is associated with the "Paresthesia" tab of the menu 752.

FIG. 7L illustrates the display 720b after a practitioner selects the "Reports" tab from the menu 752 (FIG. 7H). The display 720b illustrates a therapy report 778 having graphical representations of patient program selections and corresponding amplitude settings over time. The therapy report 778 can include multiple sections, such as a program selection graph 779, the amplitude selection graph 780, and a user-selectable key 781. The program selection graph 779 can include an x-axis 782 that shows the time and date at which program selections were maintained or changed. The program selection graph 779 can also include a y-axis 783 that shows which program was selected or that shows if no program was selected. For example, the options on the y-axis 783 can include "OFF", "Program 1", "Program 2", and "Program 3". The amplitude selection graph 780 can share the x-axis 782 of the program selection graph 779. The amplitude selection graph 780 can also have a y-axis 784 that shows the amplitude of the modulation program signal in volts, amps, millivolts, milliamps, watts, milliwatts, or the like. The combination of the program selection graph 779 and the amplitude selection graph 780 enables a practitioner to quickly preview the therapy history of the patient and can assist the practitioner in generating modifications to the therapy or in making additional recommendations for subsequent therapy. The user-selectable key 781 allows the practitioner to selectively enable or disable various aspects of the therapy report 778 for viewing. For example, by using the checkboxes in the user selectable key 781, the practitioner can cause the therapy report 778 to only display the amplitude selection graph 780, to only display the program selection graph 779, to include markers showing when one or more programs were turned off, or markers showing when low battery alerts were detected. The user selectable key 781 can also allow the practitioner to add overlays on top of the therapy report 778 to show, for example, pain levels reported by the patient and voltage levels of the battery during the time frame displayed by the x-axis 782. Additionally, the user selectable key 781 can include options that allow the practitioner to select to overlay data from other sensors, such as lead impedance detection, and/or accelerometer data.

FIG. 7M illustrates the display 720b after a practitioner selects a battery report 785 from the "Reports" tab from the menu 752 (FIG. 7H). The battery report 785 includes a battery voltage graph 786 and a battery charge time graph 787. The battery report 785 includes an x-axis 788 showing the date and/or time for the battery voltage graph 786 and the battery charge time graph 787. The battery voltage graph 786 also includes a y-axis 789 for showing parts of the battery voltage level. The units of the voltage level can be in volts, millivolts, or the like. The battery charge time graph 787 includes a y-axis 790 for plotting the amount of time the patient spends charging the battery. The battery charge time graph 787 can also include an average charge time plot 791.

The battery voltage graph 786 and the battery charge time graph 787 may be useful to the practitioner to allow the practitioner to monitor the health of the battery. If for example, the frequency of battery charging increases, the average charge time dramatically decreases, or if battery voltage levels begin to decrease dramatically faster than what is initially observed, the practitioner may determine that the battery in the signal generator has become faulty or has exceeded its useful life span. The battery report 785 can also include a user-selectable key 792 to enable the practitioner to view some or all of the graphs of the battery report 785. In some embodiments, the user selectable key 792 includes options such as the battery voltage graph 786, the battery charge time graph 787, the average charge time plot 791, the amplitude selection graph 780 of the therapy report 778, the program selection graph 779 of the therapy report 778, lead impedances, pain scores, and the like, to enable the practitioner to overlay more or less of the information collected from the signal generator while evaluating the patient's therapy history.

FIG. 7N illustrates the display 720b after a practitioner selects a lead impedance report 793 from the "Reports" tab of the menu 752. The lead impedance report 793 includes an x-axis 794 displaying time and a y-axis 795 displaying the impedance of individual contacts of the one or more leads connected to the signal generator. The lead impedance on the y-axis 795 can be in ohms, kiloohms, megaohms, or the like. The lead impedance report 793 also includes a user-selectable key 796 and selection buttons 797. The user selectable key 796 allows the practitioner to select/deselect particular ones of the contacts for display in the impedance report. The selection button 797 can include, for example, "Lead 1", "Lead 2", "P1", "P2", "P3", "Clear All", and "Select All" button options. The selection buttons 797 thereby allow the practitioner to quickly select only the contacts associated with a particular lead or a particular program for viewing. As discussed above in connection with other reports, according to various embodiments of the present disclosure, the lead impedance report 793 can be configured to overlay information from other reports, such as the therapy report and the battery report, on top of information for the lead impedance report, if desired by the practitioner.

The impedances for individual contacts can be measured in any one of a number of ways. In one example, the signal generator uses time domain reflectometry (TDR) to measure the impedance of a contact as a load. Using TDR, the signal generator transmits a high frequency pulse along the lead to the contact and measures the impedance based on the response for the signal reflected by the contact. Using TDR to measure the impedance of a contact can advantageously provide real and imaginary impedance information, such as capacitive and inductive loading. In another example, the signal generator measures the impedance of a contact by measuring the impedance between the contact under test and another contact that has been temporarily coupled to ground by the signal generator. Therefore, the signal generator can measure the impedance of a contact by measuring the impedance of the biological material of the patient that lies between the contact under test and the other contact that has been temporarily coupled to ground. In yet other examples, the signal generator can measure the impedance of a contact by measuring the impedance between the contact under test and the signal generator itself. As can be seen, various techniques can be used to measure the impedance of individual contacts, however, the practitioner may be more interested in the trends of impedance readings than the absolute impedance readings. As discussed above and shown in Table 1, an acceptable impedance reading of the contact can be between 51 ohms and 7999 ohms before a practitioner becomes alarmed about a particular malfunction, in accordance with a particular embodiment.

FIGS. 7O and 7P illustrate examples of the display 720b after the practitioner selects the "Patient Pain Scores" tab of the menu 752 of FIG. 7F. In particular, FIG. 7O illustrates the pain score screen 798 that allows the practitioner to enter and review visual analog scale (VAS) scores, i.e., levels of pain, from the patient. To create a new score, the practitioner can click a new pain score button. The practitioner can click the save button to store the new data. Entered scores can be edited or deleted by selecting the score from a list at the bottom of the pain score screen 798. The practitioner can also export the entries by selecting the export button on the pain score screen 798. According to some embodiments, the pain score screen 798 can also include an import button that imports pain scores from the implanted signal generator and displays them with corresponding time and dates in the list at the bottom of the pain score screen 798.

FIG. 7P illustrates the display 720b after a practitioner selects a quick look or graphs button on the pain score screen 798. A pain score graph 799 can provide feedback to the practitioner about the efficacy of the particular therapy. Historically, the practitioner collected VAS scores from a patient during in office visits or periodically over the telephone. However, using the various embodiments of the present disclosure, the pain score graph 799 can be populated with reports received and stored by one or more of the patient's controller, the implanted signal generator, and a server communicatively coupled to the patient's controller and the practitioner's controller. As discussed above, the patient's controller can be configured to periodically remind the patient to enter the VAS scores at particular times of the day, when a patient changes a modulation program, or when the signal generator detects a particular set of events (e.g., substantial change in lead impedance, etc.). The pain score graph can include an x-axis 800 and a y-axis 801. The x-axis 800 can show the time and date of various VAS score entries, and the y-axis 801 can show the intensity of the VAS scores. For example, the VAS scores on the y-axis 801 can range from 0 for no pain to 10 for very severe or worst pain. Because the patient's controller can receive VAS score entries, the practitioner or the practitioner's controller can determine the efficacy of various modulation programs and can determine the rate at which individual programs effectively deliver pain reducing therapy.

The pain score graph 799 can also include an alternative view 802 of the pain score graph to allow the practitioner to see more or fewer days than are shown by the x-axis 800. As described above, the pain score graph 799 can overlay one or more of the other graphs, e.g., the battery voltage graph 786, the program selection graph 779, the lead impedance report 793, to provide the practitioner with a holistic view of the status of the patient and the therapy delivery system at any given point in time. Such an overlay view of multiple graphs can allow the practitioner to troubleshoot potential errors in the signal generator, in the signal delivery leads, and the battery. The overlay view can also assist the practitioner in diagnosing other medical conditions of the patient, such as stroke, seizure, or myocardial infarction.

FIG. 7Q illustrates the display 720b after the practitioner selects the "Paresthesia Testing" tab from the menu 752. The paresthesia testing interface 803 allows the practitioner to initially test the patient's physical response to various settings. The paresthesia testing interface 803 can include selectable contacts settings 804, a frequency setting 805, a pulse width setting 806, and an amplitude setting 807. The practitioner can use these various setting to generate a test modulation program signal. Various additional buttons such as a start button 808, a stop button 809, and a save button 810 can be used to start and stop the test modulation program signal and save the parameters of the test modulation program signal, if desired.

Figure 8:
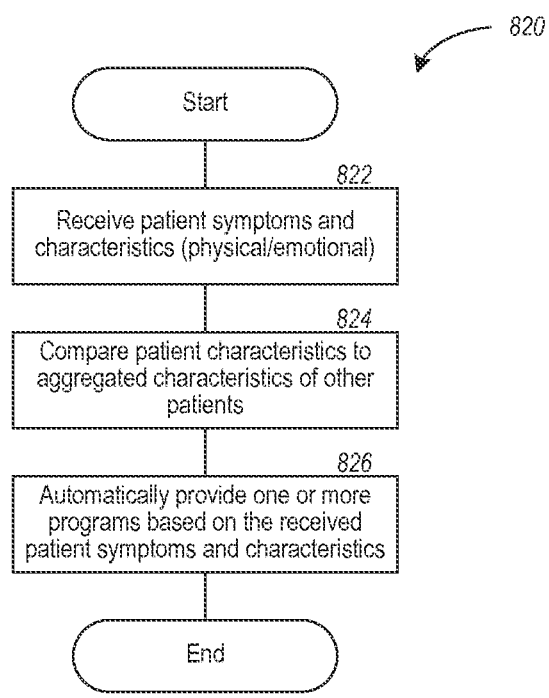
FIG. 8 is a flow diagram illustrating a method of operating a practitioner-operated controller in accordance with a particular embodiment of the present disclosure.

FIG. 8 illustrates a method 820 of operating a practitioner's controller. At block 822 the practitioner's controller receives patient symptoms and characteristics. The patient's symptoms and characteristics can include age, weight, medications taken, symptoms, and locations of symptoms. The patient's controller can receive the patient's symptoms and characteristics from the practitioner, or can download the symptoms and characteristics directly from the patients signal generator. At block 824 the practitioner's controller can compare patient characteristics to the aggregated characteristics of other patients. At block 826, the practitioner's controller can automatically provide one or more programs to the practitioner based on the received patient symptoms and characteristics. The practitioner's controller can download modulation programs with corresponding characteristics of other patients from a server, such as server 204 of FIG. 2. Alternatively, the practitioner's controller can locally execute a database or other search table to store, organize, and/or sort patients' information with modulation programs that have been rated or ranked as being effective for patients having similar characteristics and symptoms.

The overall program can automatically take advantage of information that indicates a successful modulation location and can generate backup parameters which include, but are not limited to, backup contact locations. The backup locations can be automatically implemented, e.g., if the lead were to move. For example, the program can automatically track how long the patient uses different modulation programs and, based upon the assumption that the patient will use successful modulation programs more often than unsuccessful modulation programs, can rank the modulation programs. If the contacts associated with a particularly successful modulation program become unavailable (e.g., due to the lead shifting or an impedance change in the lead), the system can automatically select the next-best set of modulation parameters. In another embodiment, the patient and/or a practitioner can manually bracket the vertebral levels over which the system can select alternative sets of modulation parameters. In still further embodiments, the patient can directly input data that identifies which modulation programs are most desirable.

Particular embodiments of the foregoing systems and processes can produce one or more of several advantages. For example, by automating these processes, the amount of time required for accurately selecting signal delivery parameters can be reduced, thereby increasing the number of patients who can be treated in a given period of time. In addition, the automated techniques can take advantage of large quantities of patient data to establish signal delivery parameters for a particular patient, in a manner that would be cumbersome, unwieldy, and/or very time consuming if it were performed by an individual practitioner. One or more aspects of the present disclosure include computer-readable media having instructions, which when executed, perform one or more of the above-described features, programs, displays, and/or protocols.

6.0 Representative Modulation Locations and Indications

Many of the embodiments described above were described in the context of treating chronic, neuropathic low back pain with modulation signals applied to the lower thoracic vertebrae (T9-T12). In other embodiments, modulation signals having parameters (e.g., frequency, pulse width, amplitude, and/or duty cycle) generally similar to those described above can be applied to other patient locations to address other indications. For example, while the foregoing methodologies included applying modulation at lateral locations ranging from the spinal cord midline to the DREZ, in other embodiments, the modulation may be applied to the foramen region, laterally outward from the DREZ. In other embodiments, the modulation may be applied to other spinal levels of the patient. For example, modulation may be applied to the sacral region and more particularly, the "horse tail" region at which the sacral nerves enter the sacrum. Urinary incontinence and fecal incontinence represent example indications that are expected to be treatable with modulation applied at this location. In other embodiments, the modulation may be applied to other thoracic vertebrae. For example, modulation may be applied to thoracic vertebrae above T9. In a particular embodiment, modulation may be applied to the T3-T6 region to treat angina. Modulation can be applied to high thoracic vertebrae to treat pain associated with shingles. Modulation may be applied to the cervical vertebrae to address chronic regional pain syndrome and/or total body pain, and may be used to replace neck surgery. Suitable cervical locations include vertebral levels C3-C7, inclusive. In other embodiments, modulation may be applied to the occipital nerves, for example, to address migraine headaches.

As described above, modulation in accordance with the foregoing parameters may also be applied to treat acute and/or chronic nociceptive pain. For example, modulation in accordance with these parameters can be used during surgery to supplement and/or replace anesthetics (e.g., a spinal tap). Such applications may be used for tumor removal, knee surgery, and/or other surgical techniques. Similar techniques may be used with an implanted device to address postoperative pain, and can avoid the need for topical lidocaine. In still further embodiments, modulation in accordance with the foregoing parameters can be used to address other peripheral nerves. For example, modulation can be applied directly to peripheral nerves to address phantom limb pain.

Still further embodiments of representative therapies and indications are included in the following U.S. applications, each of which is incorporated herein by reference: Ser. Nos. 12/264,836; 12/703,683; 12/765,790; 12/765,747; and 13/607,617.

The methods disclosed herein include and encompass, in addition to methods of making and using the disclosed devices and systems, methods of instructing others to make and use the disclosed devices and systems. For example, a method in accordance with a particular embodiment includes receiving a first input corresponding to a location of a signal delivery device implanted in a patient, establishing a positional relationship between the implanted signal delivery device and an anatomical feature of the patient, receiving a second input corresponding to a medical indication of the patient, and, based at least in part on the positional relationship and the indication, automatically identifying a signal delivery parameter in accordance with which a pulsed electrical signal is delivered to the patient via the signal delivery device. Accordingly, any and all methods of use and manufacture disclosed herein also fully disclose and enable corresponding methods of instructing such methods of use and manufacture. Methods of instructing such use and manufacture may take the form of computer-readable-medium-based executable programs or processes.

7.0 Representative Embodiments

In one embodiment, a computer-readable medium includes instructions for a server of implantable medical device data. The instructions, when executed by the server, can cause the server to receive the implantable medical device data for implantable medical devices associated with a plurality of patients. The implantable medical device data can include characteristics of the patients and symptoms described by the patients. Individual implantable medical devices can include an implantable signal generator, and an elongated signal delivery lead attachable to the implantable signal generator and positionable proximate to each patient's spinal cord. The instructions can cause the server to receive, from multiple computing devices, ratings for modulation programs executed by the implantable medical devices for the plurality of patients, with individual modulation programs being associated with generating a signal via a corresponding one of the implantable medical devices, the signal having a frequency, a duty cycle, and a range of amplitudes, and the signal being directed to contacts of at least one of the elongated signal delivery leads. The instructions can also cause the server to rank the modulation programs based on the received ratings and based on at least one of the characteristics of the patients and the symptoms described by the patients. Furthermore, the instructions can cause the server to receive a recommendation request for a modulation program for a particular patient; and transmit one or more of the highest ranking modulation programs in response to the request for a modulation program for the particular patient.

The ratings for the modulation programs can correspond to levels of pain experienced by the patients while using the implantable medical devices, and the rating can be inversely correlated with the level of pain in patient. The instructions can further cause the server to host a webpage that provides a graphical interface of the ratings for each modulation program, and the graphical interface can present statistical relationships between the modulation programs and levels of pain experienced by the patients. In some embodiments, the graphical interface can display statistical relationships between the modulation programs, levels of pain experienced by the patients, and locations of sources of pain for the patients. In several embodiments, the signal can be delivered to one contact from the elongated signal delivery lead.

The characteristics of the patients can include an age, a weight, and a height of an individual patient; and the symptoms described by the patients can include a level of pain and a location of pain. The implantable medical device data received by the server can include levels of activity for the plurality of patients. The computing devices can include an implantable medical device programmer used by a physician, a cellular telephone used by an individual patient, or an implantable medical device controller used by an individual patient.

In another embodiment, a patient therapy system includes a wireless interface operable to transmit modulation programs to an implantable signal generator. The implantable signal generator can be attached to one or more implantable elongated signal delivery devices that are positionable proximate to a patient's spinal cord. The therapy system can also include a display operable to graphically represent the modulation programs. A computer-readable medium can include instructions for determining and displaying the modulation programs, as well as a processor coupled to the computer-readable medium to execute the instructions. The instructions can cause the patient therapy system to display programming characteristics of at least two modulation programs concurrently on the display at a graphical user interface. The programming characteristics for individual modulation programs can include identifiers for electrode contacts of the one or more implantable elongated signal delivery devices, and amplitude ranges for signals generated between the identified electrode contacts. At least one modulation program can include an identifier for a first pair of contacts corresponding to a first location relative to the patient's spinal cord, and a second pair of contacts corresponding to a second location relative to the patient's spinal cord.

The instructions of the patient therapy system can further cause the patient therapy system to provide a program input control to enable a user to add an additional modulation program to the graphical user interface. The programming characteristics can further include frequencies for the signals, duty cycles for the signals, or anode and cathode assignments for the electrode contacts. The instructions can further cause the patient therapy system to provide a programming characteristics control at the graphical user interface to enable a user to selectively switch between displaying a first portion of the programming characteristics and a second portion of the programming characteristics, for each of the modulation programs. In some embodiments, the second portion of the programming characteristics displays a plurality of user selectable characteristics including: frequencies for the signals; pulse widths for the signals; on-times for the signals (where the on-times correspond to a duration for an individual series of pulse cycles); and duty cycles for the signals (where the duty cycles correspond to a percentage of a total amount of time that any pulse cycles are delivered).

In yet another embodiment, a patient therapy system includes a wireless interface operable to receive usage data and modulation programs from an implantable signal generator. The implantable signal generator can be attachable to one or more implantable elongated signal delivery devices that are positionable proximate to a patient's spinal cord. The patient therapy system can further include: a) a display operable to graphically represent the usage data received from the implantable signal generator; b) a computer-readable medium having instructions for generating multiple graphs based on the usage data; c) a processor coupled to the wireless interface, coupled to the display, and coupled to the computer-readable medium to execute the instructions to cause the patient therapy system to render, at the display, one or more of the multiple graphs. The multiple graphs can include a program selection graph and an amplitude selection graph. The program selection graph can include a time axis and a modulation program axis, the modulation program axis indicating which of the modulation programs the implantable signal generator executed at a particular time and date, as indicated by the time axis, the modulation program axis indicating when the implantable signal generator stopped executing any of the modulation programs. The amplitude selection graph can include a time axis and an amplitude axis, the amplitude axis representing an intensity with which one of the implantable signal generators delivered a modulation signal to the one or more implantable elongated signal delivery devices. The program selection graph can be rendered concurrently with the amplitude selection graph.

The wireless interface can receive diagnostic data from the implantable signal generator, the diagnostic data including impedance measurements for electrode contacts on the one or more implantable elongated signal delivery devices. The implantable signal generator can generate the impedance measurements with reference to the implantable signal generator, and individual impedance measurements can be correlated with an impedence between a respective one of the electrode contacts and the implantable signal generator. The usage data can include levels of charge of a battery in the implantable signal generator. The instructions can cause the patient therapy system to render, at the display, a battery charge graph illustrating levels of charge of the battery with respect to a time axis. The instructions can also cause the patient therapy system to render, at the display, a charge time graph illustrating lengths of time the battery was charged, based on the usage data. The instructions can include instructions for diagnosing a battery malfunction based on the levels of charge of the battery and based on the lengths of time the battery was charged.

In several embodiments, the patient therapy system can include a network interface coupled to the processor and operable to receive medication usage data for the patient. The multiple graphs can include a medication graph that illustrates one or more levels of medication usage with respect to time during use of the implantable signal generator. The network interface can receive medication usage data from at least one of the patient's cellular telephone, the patient's implantable signal generator, or a server storing the patient's medication useage data during the patient's use of the implantable signal generator. The usage data can include activity level data of the patient based on a motion sensor within the implantable signal generator, and the multiple graphs can include an activity graph that illustrates activity levels of the patient with respect to time, based on the activity level data. The motion sensor can be an accelerometer, the activity level data can indicate a postural position of the patient, and the activity level graph can illustrate the postural position of the patient (including lying down, standing up, and partially reclined). The network interface can be operable to receive the pain score data from at least one of the patient's cellular telephone, the patient's implantable signal generator controller, or a server storing the patient's uploaded pain score associated with the patient's use of the implantable signal generator.

From the foregoing, it will be appreciated that specific embodiments of the present disclosure have been described herein for purposes of illustration, but that various modifications may be made without deviating from the present disclosure. For example, the specific parameter ranges and indications described above may be different in further embodiments. As described above, the practitioner can avoid the use of certain procedures, (e.g., mapping, trial periods and/or current steering), but in other embodiments, such procedures may be used in particular instances. The lead described above with reference to FIGS. 7B-7H can have more than two groups of contacts, and/or can have other contact spacings in other embodiments. In some embodiments, as described above, the signal amplitude applied to the patient can be constant. In other embodiments, the amplitude can vary in a preselected manner, e.g., via ramping up/down, and/or cycling among multiple amplitudes. The signal delivery elements can have an epidural location, as discussed above with regard to FIG. 1B, and in other embodiments, can have an extradural location. In particular embodiments described above, signals having the foregoing characteristics are expected to provide therapeutic benefits for patients having low back pain and/or leg pain, when modulation is applied at vertebral levels from about T9 to about T12. In at least some other embodiments, it is believed that this range can extend from about T5 to about L1. Certain processes may be described in the context of multiple inputs, e.g., first, second, and third inputs to a physician's controller. These inputs may vary from one embodiment to another.

Certain aspects of the present disclosure described in the context of particular embodiments may be combined or eliminated in other embodiments. For example, as described above, the trial period, operating room mapping process, and/or external modulator may be eliminated or simplified in particular embodiments. Therapies directed to particular indications may be combined in still further embodiments. Further, while advantages associated with certain embodiments have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

I claim:

1. A patient therapy system, comprising:
    a wireless interface operable to receive usage data and modulation programs from an implantable signal generator, the implantable signal generator attachable to one or more implantable elongated signal delivery devices that are positionable proximate to a patient's spinal cord to deliver electrical stimulation signals;
    a display operable to graphically represent the usage data received from the implantable signal generator;

a computer-readable medium having instructions for generating multiple graphs based on the usage data;

a processor coupled to the wireless interface, coupled to the display, and coupled to the computer-readable medium to execute the instructions to cause the patient therapy system to render, at the display, one or more of the multiple graphs, wherein the multiple graphs include a program selection graph and an amplitude selection graph, wherein the program selection graph includes a time axis and a modulation program axis, the modulation program axis indicating which of the modulation programs the implantable signal generator executed at a particular time and date, as indicated by the time axis, the modulation program axis indicating when the implantable signal generator stopped executing any of the modulation programs, wherein the amplitude selection graph includes a time axis and an amplitude axis, the amplitude axis representing an intensity with which the implantable signal generator delivered particular electrical stimulation signals to the one or more implantable elongated signal delivery devices, and wherein the program selection graph is rendered concurrently with the amplitude selection graph.

2. The patient therapy system of claim 1 wherein the wireless interface receives diagnostic data from the implantable signal generator, the diagnostic data including impedance measurements for electrode contacts on the one or more implantable elongated signal delivery devices.

3. The patient therapy system of claim 2 wherein the implantable signal generator generates the impedance measurements with reference to the implantable signal generator, individual impedance measurements being correlated with an impedance between a respective one of the electrode contacts and the implantable signal generator.

4. The patient therapy system of claim 1 wherein the usage data includes levels of charge of a battery in the implantable signal generator.

5. The patient therapy system of claim 4 wherein the instructions further cause the patient therapy system to render, at the display:

a battery charge graph illustrating the levels of charge of the battery with respect to a time axis; and a charge time graph illustrating lengths of time the battery was charged, based on the usage data.

6. The patient therapy system of claim 5 wherein the instructions include instructions for diagnosing a battery malfunction based on the levels of charge of the battery and based on the lengths of time the battery was charged.

7. The patient therapy system of claim 6, further comprising a network interface coupled to the processor and operable to receive medication usage data for the patient, the multiple graphs including a medication graph that illustrates one or more levels of medication usage with respect to time during use of the implantable signal generator.

8. The patient therapy system of claim 7 wherein the network interface receives the medication usage data from at least one of a cellular telephone, the implantable signal generator, or a server storing the patient's medication usage data during the patient's use of the implantable signal generator.

9. The patient therapy system of claim 1 wherein the usage data includes activity level data of the patient based on a motion sensor within the implantable signal generator, the multiple graphs including an activity graph that illustrates activity levels of the patient with respect to time, based on the activity level data.

10. The patient therapy system of claim 9 wherein the motion sensor is an accelerometer, the activity level data indicating a postural position of the patient, the activity level graph further illustrating the postural position of the patient, the postural position of the patient including lying down, standing up, and partially reclined.

11. The patient therapy system of claim 1, further comprising a network interface coupled to the processor and operable to receive pain score data from at least one of a cellular telephone, a controller for the implantable signal generator, or a server storing the patient's received pain score associated with the patient's use of the implantable signal generator.

* * * * *